US012714411B2

(12) United States Patent
Considine et al.

(10) Patent No.: US 12,714,411 B2
(45) Date of Patent: Aug. 25, 2026

(54) RETRACTOR FOR SURGICAL PROCEDURES

(71) Applicant: Alphatec Spine, Inc., Carlsbad, CA (US)

(72) Inventors: David Considine, Torrington, CT (US); Andrew W. Rajek, Escondido, CA (US); Maximilian Garcia, Encinitas, CA (US); Ethan Padgett, Carlsbad, CA (US); Alexis Fiechtner, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 128 days.

(21) Appl. No.: 18/636,256

(22) Filed: Apr. 15, 2024

(65) Prior Publication Data

US 2025/0318820 A1 Oct. 16, 2025

(51) Int. Cl.
*A61B 17/02* (2006.01)
*A61B 90/50* (2016.01)

(52) U.S. Cl.
CPC .......... *A61B 17/0206* (2013.01); *A61B 90/50* (2016.02)

(58) Field of Classification Search
CPC .................................................. A61B 17/0206
See application file for complete search history.

(56) References Cited

U.S. PATENT DOCUMENTS 4,834,112 A 5/1989 Machek et al.
5,616,117 A * 4/1997 Dinkler .............. A61B 17/0206 600/210
5,795,291 A 8/1998 Koros et al.
5,882,298 A 3/1999 Sharratt
5,928,139 A 7/1999 Koros et al.
6,042,540 A * 3/2000 Johnston ............ A61B 17/0206 600/219
6,733,444 B2 * 5/2004 Phillips .............. A61B 17/0206 600/213
6,887,197 B2 * 5/2005 Phillips .............. A61B 17/0206 600/201
6,945,933 B2 9/2005 Branch et al.
7,473,223 B2 * 1/2009 Fetzer .................... A61B 90/50 292/199

(Continued)

FOREIGN PATENT DOCUMENTS

DE 202009005768 U1 6/2009
DE 202020003344 U1 8/2020

(Continued)

OTHER PUBLICATIONS

Jul. 8, 2025 ISR & WO.

(Continued)

*Primary Examiner* — Jacqueline T Johanas

(74) *Attorney, Agent, or Firm* — Dentons Durham Jones Pinegar; Sarah W. Matthews; Lilly Godfrey

(57) ABSTRACT

A retractor may include a proximal portion and a distal portion opposite the proximal portion. The distal portion may include first and second blade retractors each having a blade receptacle defined in a first end of a body. The blade receptacle has an opening that narrows to a seat for receiving a blade head, the seat defining a shape that reduces translation, rotation, and/or angulation of the blade head.

19 Claims, 24 Drawing Sheets

(56) References Cited

U.S. PATENT DOCUMENTS 7,582,058 B1 9/2009 Miles et al.
7,588,537 B2 * 9/2009 Bass .................... A61B 17/02 600/210
7,785,253 B1 8/2010 Arambula et al.
8,137,284 B2 3/2012 Miles et al.
8,357,087 B2 * 1/2013 Fetzer .................. A61B 90/50 600/213
8,876,709 B2 11/2014 Vayser et al.
8,900,137 B1 12/2014 Lovell et al.
8,974,381 B1 3/2015 Lovell et al.
9,028,522 B1 5/2015 Prado
9,113,853 B1 8/2015 Casey et al.
9,277,906 B2 3/2016 White
9,414,828 B2 8/2016 Abidin et al.
9,848,862 B2 * 12/2017 Bass .................... A61B 17/02
10,149,674 B2 * 12/2018 Angus ................ A61B 17/0206
10,363,022 B2 * 7/2019 Serokosz ........... A61B 17/7077
10,426,454 B2 10/2019 Ponmudi et al.
10,448,941 B2 10/2019 Daavettila et al.
2003/0120132 A1 * 6/2003 Phillips ............. A61B 17/0206 600/210
2003/0191370 A1 * 10/2003 Phillips ............. A61B 17/0206 600/201
2004/0087833 A1 5/2004 Bauer et al.
2006/0178566 A1 * 8/2006 Fetzer .................. A61B 90/50 600/234
2007/0055110 A1 3/2007 Bass
2009/0227845 A1 9/2009 Lo et al.
2010/0081885 A1 4/2010 Wing et al.
2010/0222644 A1 9/2010 Sebastian et al.
2012/0271119 A1 * 10/2012 White ............... A61B 17/0206 600/228
2012/0323080 A1 12/2012 Deridder et al.
2013/0261401 A1 10/2013 Hawkins et al.
2014/0172002 A1 6/2014 Predick
2014/0336471 A1 11/2014 Pfabe et al.
2015/0351738 A1 12/2015 Perrow
2016/0192922 A1 7/2016 Friedrich et al.
2016/0317137 A1 11/2016 Predick et al.
2017/0143325 A1 5/2017 Lynn et al.
2017/0231613 A1 8/2017 Casey et al.
2017/0238918 A1 8/2017 Predick et al.
2017/0311941 A1 11/2017 Daavettila et al.
2017/0333023 A1 11/2017 Adams
2019/0021715 A1 1/2019 O'Connell et al.
2019/0110785 A1 * 4/2019 Serokosz ........... A61B 17/0206
2019/0142480 A1 5/2019 Woolley et al.
2019/0298327 A1 * 10/2019 Serokosz ............ A61B 17/025
2019/0298328 A1 10/2019 Popejoy et al.
2019/0307439 A1 10/2019 Chhit et al.
2020/0015799 A1 1/2020 Tsubouchi
2021/0085306 A1 3/2021 Clauss et al.
2023/0013570 A1 1/2023 White et al.
2023/0380871 A1 * 11/2023 Gelber ............... A61B 17/0206
2024/0260956 A1 * 8/2024 Casey .................... A61B 17/02
2024/0350129 A1 * 10/2024 McClymont ........... A61B 90/57
2025/0082316 A1 * 3/2025 Serra .................. A61B 17/0206
2025/0318820 A1 * 10/2025 Considine .......... A61B 17/0206

FOREIGN PATENT DOCUMENTS

EP 3626189 A1 * 3/2020 ......... A61B 17/8872
WO WO-2008039427 A2 * 4/2008 ......... A61B 17/0206
WO 2016153942 A1 9/2016
WO 2019055173 A1 3/2019

OTHER PUBLICATIONS

International Search Report and Written Opinion from PCTUS2025204428, Jul. 8, 2025.
International Preliminary Report on Patenability from related pending international application PCT/US2022/028132, dated Oct. 24, 2023.
Search Report of the International Searching Authority from related pending international application PCT/US2022/028132, dated Oct. 24, 2023.
Written Opinion of the International Searching Authority from related pending international application PCT/US2022/028132, dated Oct. 24, 2023.

* cited by examiner

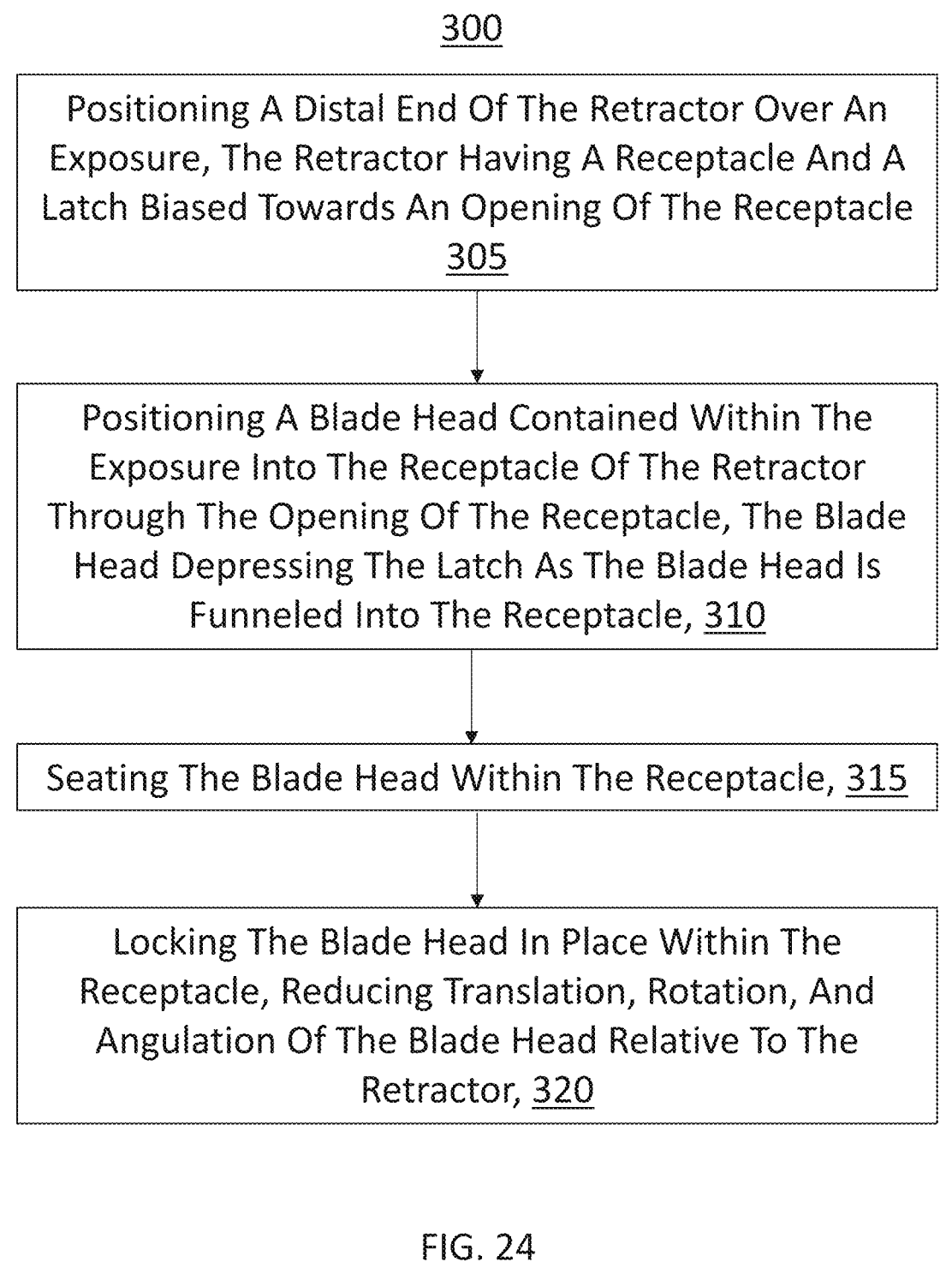

300

Positioning A Distal End Of The Retractor Over An Exposure, The Retractor Having A Receptacle And A Latch Biased Towards An Opening Of The Receptacle 305

Positioning A Blade Head Contained Within The Exposure Into The Receptacle Of The Retractor Through The Opening Of The Receptacle, The Blade Head Depressing The Latch As The Blade Head Is Funneled Into The Receptacle, 310

Seating The Blade Head Within The Receptacle, 315

Locking The Blade Head In Place Within The Receptacle, Reducing Translation, Rotation, And Angulation Of The Blade Head Relative To The Retractor, 320

FIG. 24

RETRACTOR FOR SURGICAL PROCEDURES

TECHNICAL FIELD

This disclosure relates generally to engagement mechanisms used by retractors for use in surgical procedures. More specifically, this disclosure relates to retractors for use in spinal procedures.

SUMMARY

Disclosed are systems, devices, and/or methods of use thereof regarding retractors for use in surgical procedures, such as spinal procedures. In various aspects, a retractor includes a proximal portion having a rack and pinion mechanism in connection with a first cabin and a second cabin such that the first and second cabins are independently retractable along the rack. The rack may have a first adaptor on a first end and a second adaptor on a second end, where the first and second adaptors are for selectively connecting the rack to a table-mounted surgical arm. The retractor also includes a distal portion opposite the proximal portion. The distal portion may be connected to the proximal portion through a first arm in connection with the first cabin and a second arm in connection with the second cabin. The distal portion may include a first blade engagement in connection with the first arm and a second blade engagement in connection with the second arm. Each of the first and second blade engagements may include a substantially L-shaped body in connection with the first arm or second arm, respectively, and a receptacle defined in a first end of the L-shaped body. The receptacle may have an hourglass shape for receiving a blade head. Each of the first and second blade engagements may also include a latch for covering a portion of the receptacle upon receipt of the blade head, an adaptor at a second end of the L-shaped body for selectively connecting the distal portion to a table-mounted surgical arm, a release latch for retracting the latch to reduce translation of the blade head, and an angulation knob adjacent to the adaptor at the second end of the L-shaped body, the angulation knob for rotating the L-shaped body.

In various aspects, a retractor may include a proximal portion and a distal portion opposite the proximal portion. The distal portion may include a first blade engagement having a blade receptacle defined in a first end of a body of the first blade retractor. The blade receptacle may have an opening that narrows to a seat for receiving a blade head, where the seat defines a shape that receives the shaped blade head to reduce translation, rotation, and/or angulation of the blade head. The distal portion may also include a second blade engagement having a blade receptacle defined in a first end of a body of the second blade engagement. The blade receptacle may have an opening that narrows to a seat for receiving a shaped blade head, where the seat defines a shape that reduces translation, rotation, and/or angulation of the shaped blade head.

In various aspects, a method of assembling a blade to a retractor may include positioning a distal end of the retractor over an exposure, with the retractor having a receptacle and a latch biased towards an opening of the receptacle. The method may also include funneling a blade head of a retractor blade already contained within the exposure into the receptacle of the retractor through the opening of the receptacle, the blade head depressing the latch as the blade head is funneled into the receptacle. Additionally, the method may include seating the blade head within the receptacle and locking the blade head within the receptacle when the latch returns to its biased position across the opening of the receptacle, reducing translation, rotation, and angulation of the blade head relative to the retractor.

Other aspects of the disclosed subject matter, as well as features and advantages of various aspects of the disclosed subject matter, should be apparent to those of ordinary skill in the art through consideration of the ensuing description, the accompanying drawings, and the appended claims.

BRIEF DESCRIPTION OF THE DRAWINGS

In the drawings:

FIG. 24 is a flowchart of one example method of using or assembling the retractor of FIG. 1 with a blade head.

DETAILED DESCRIPTION

Figure 1:
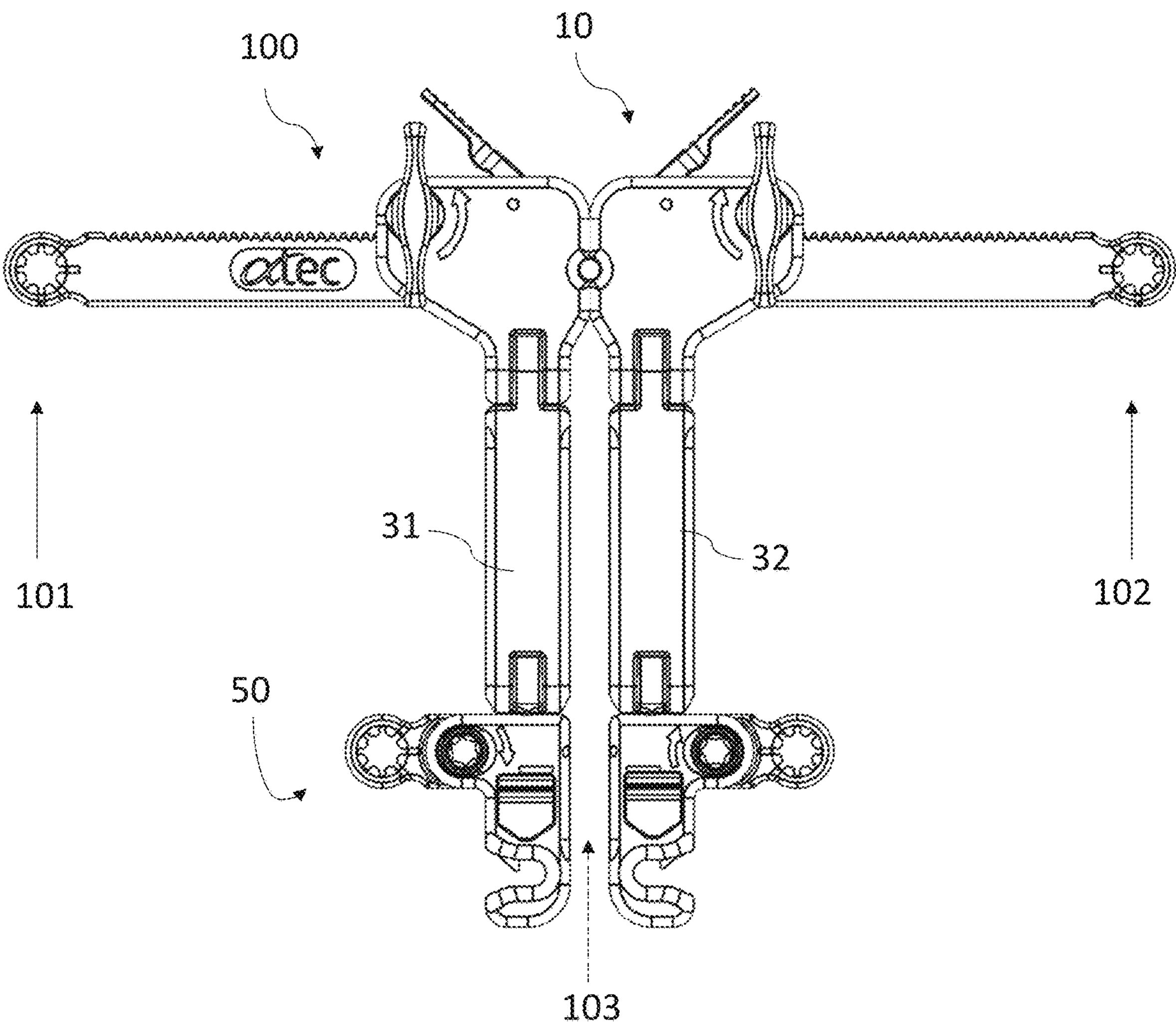
FIG. 1 illustrates a top view of a retractor.
Figure 2:
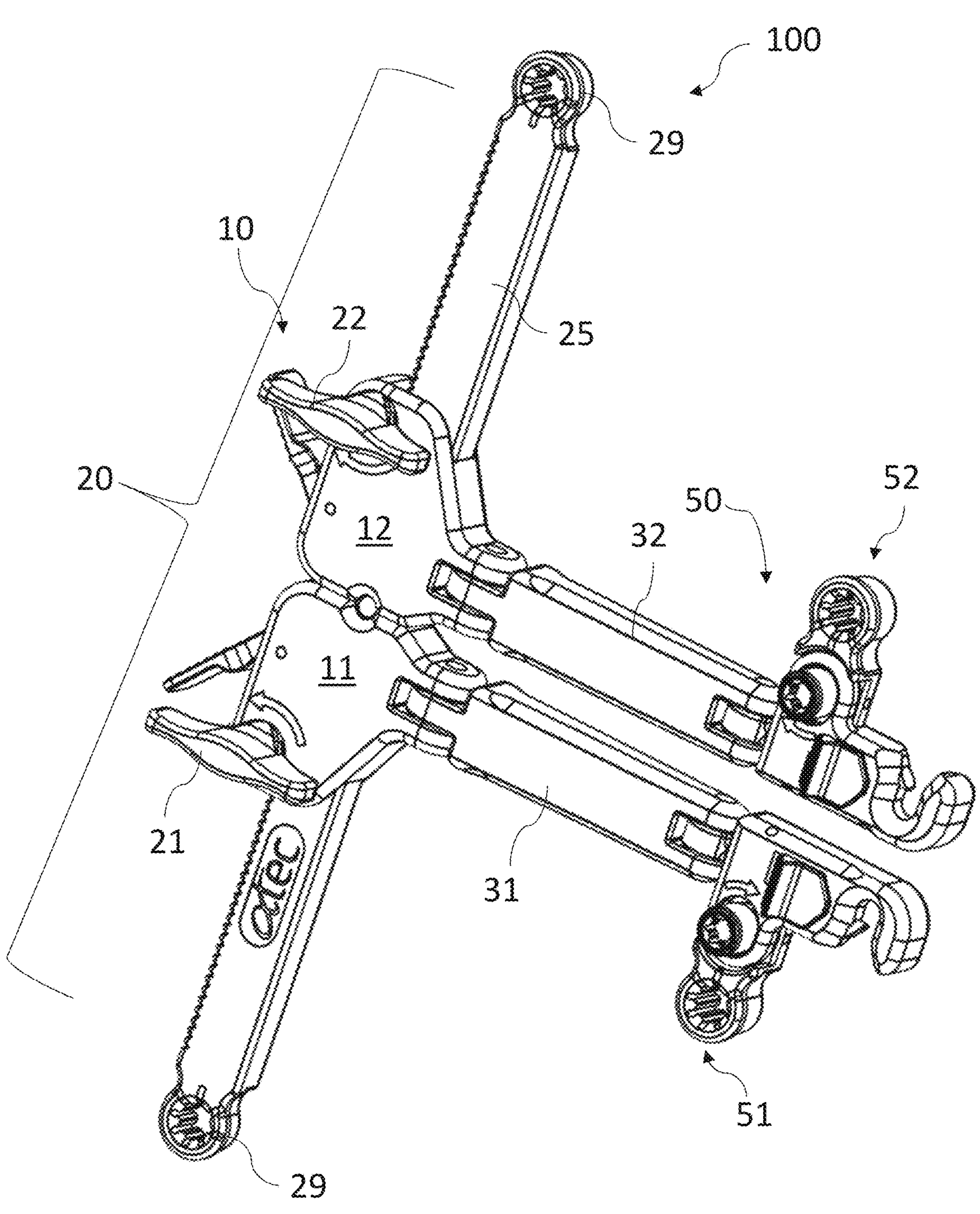
FIG. 2 illustrates a top, perspective view of the retractor of FIG. 1.

Retractors are commonly used in surgical procedures, such as in spinal disc removal or replacement surgeries. During spinal surgeries, a surgeon will access the area to be worked on through an exposure. Importantly, the exposure must be kept clear and open for the surgeon or other practitioner to perform the procedure. Generally, keeping the exposure clear and open requires the surgeon or other practitioner to hold patient anatomy (e.g., esophagus, etc.) in place and out of the surgeon's way, such as by moving the patient anatomy to one side of the exposure. This can be done by hand (i.e., the surgeon or other practitioner physically holds the esophagus out of the way) or with simplified instruments.

Retractors are used to both hold patient anatomy and surgical instruments out of the way of the exposure, so the surgeon or other practitioner can successfully perform the procedure.

FIGS. 1 through 4 illustrate views of a retractor 100. The retractor 100 includes a proximal portion 10 and a distal portion 50 opposite the proximal portion 10. The distal portion 50 is connected to the proximal portion 10 through arms 31, 32. The retractor 100 has a medial or center line 103 and opposing lateral sides 101, 102.

The proximal portion 10 of the retractor 100 includes a first cabin 11, a second cabin 12, and a rack-and-pinion mechanism 20. The rack and pinion mechanism 20 includes a rack 25 that is receivable within the first cabin 11 and the second cabin 12, a first pinion 21, and a second pinion 22. The first and second cabins 11, 12 may be actuated or retracted along a length of the rack 25 through the first pinion 21 and the second pinion 22, respectively.

Figure 3:
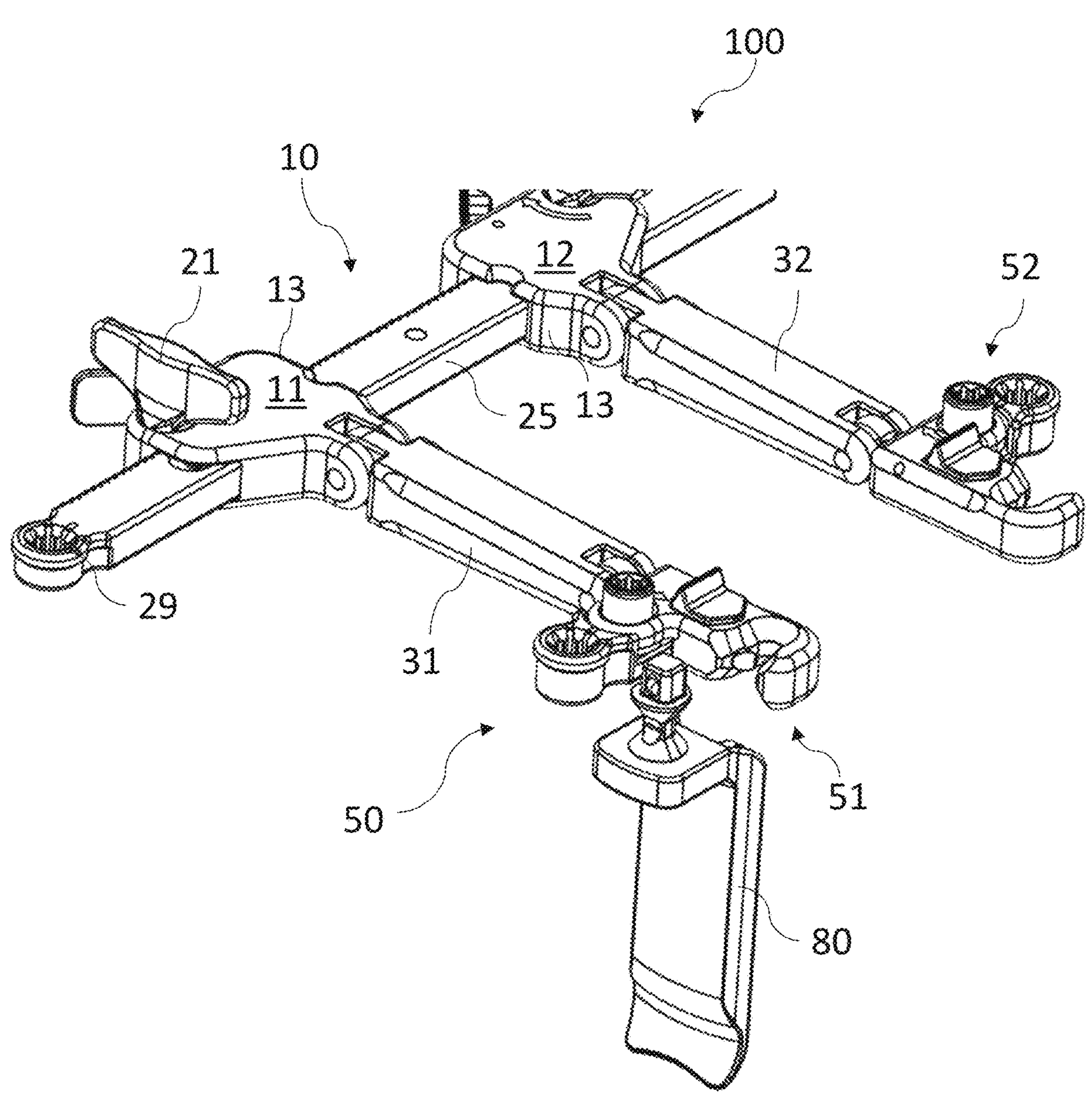
FIG. 3 illustrates a side, perspective view of the retractor of FIG. 1 and a blade with a blade head to be attached to the retractor.

For example, as shown in FIG. 3, the first cabin 11 and the second cabin 12 may be retracted along the rack 25 towards lateral sides 101, 102 of the retractor 100. Specifically, the first cabin 11 may be retracted towards lateral side 101 and the second cabin 12 may be retracted towards lateral side 102. The first and second pinions 21, 22 may be actuated or rotated to effectuate retraction of the first and second cabins 11, 12 along the rack 25.

The distal portion 50 includes a first blade engagement 51 in connection with the first cabin 11 through a first arm 31, and a second blade engagement 52 in connection with the second cabin 12 through a second arm 32. Retraction of the first and second cabins 11, 12 along the rack 25 also moves the first and second blade engagements 51, 52 towards respective lateral sides 101, 102 of the retractor 100.

Figure 4:
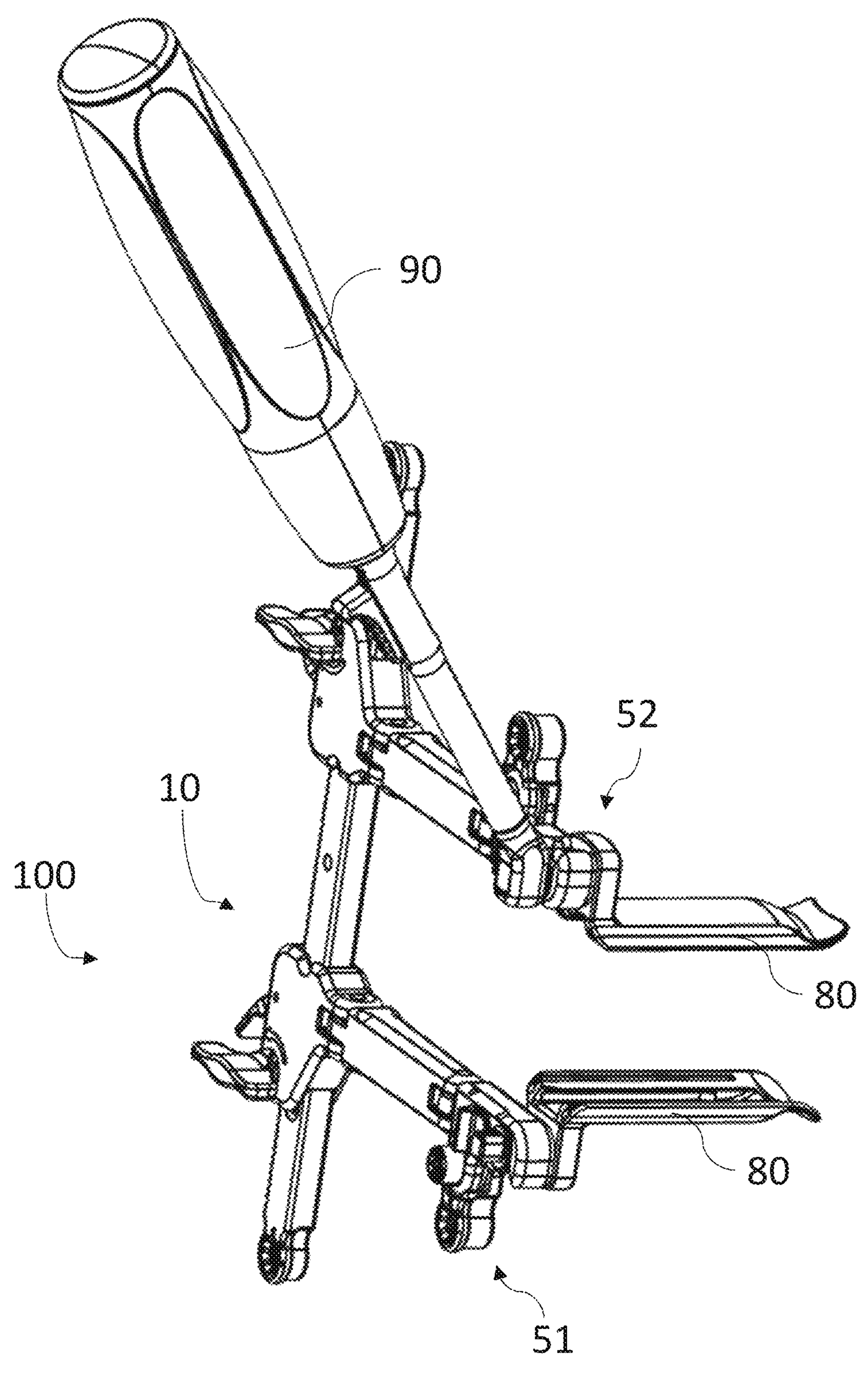
FIG. 4 illustrates an end view of the retractor of FIG. 1 having blades assembled in the retractor and a handle attached to a head of one of the blades to facilitate blade placement.

The first blade engagement 51 may be a substantially mirror image of the second blade engagement 52. The first and second blade engagements 51, 52 each are for receiving and holding a blade head of a blade 80. Additionally, as explained more herein, the first and second blade engagements 51, 52 each are for holding the blade 80 out of the way of the practitioner performing a surgery to provide a clear surgical field. As shown in FIG. 4, the blade heads of the blades 80 may be attachable to a handle 90, which may allow positioning or leverage of the blades 80 or the retractor 100 during a procedure.

Figure 5:
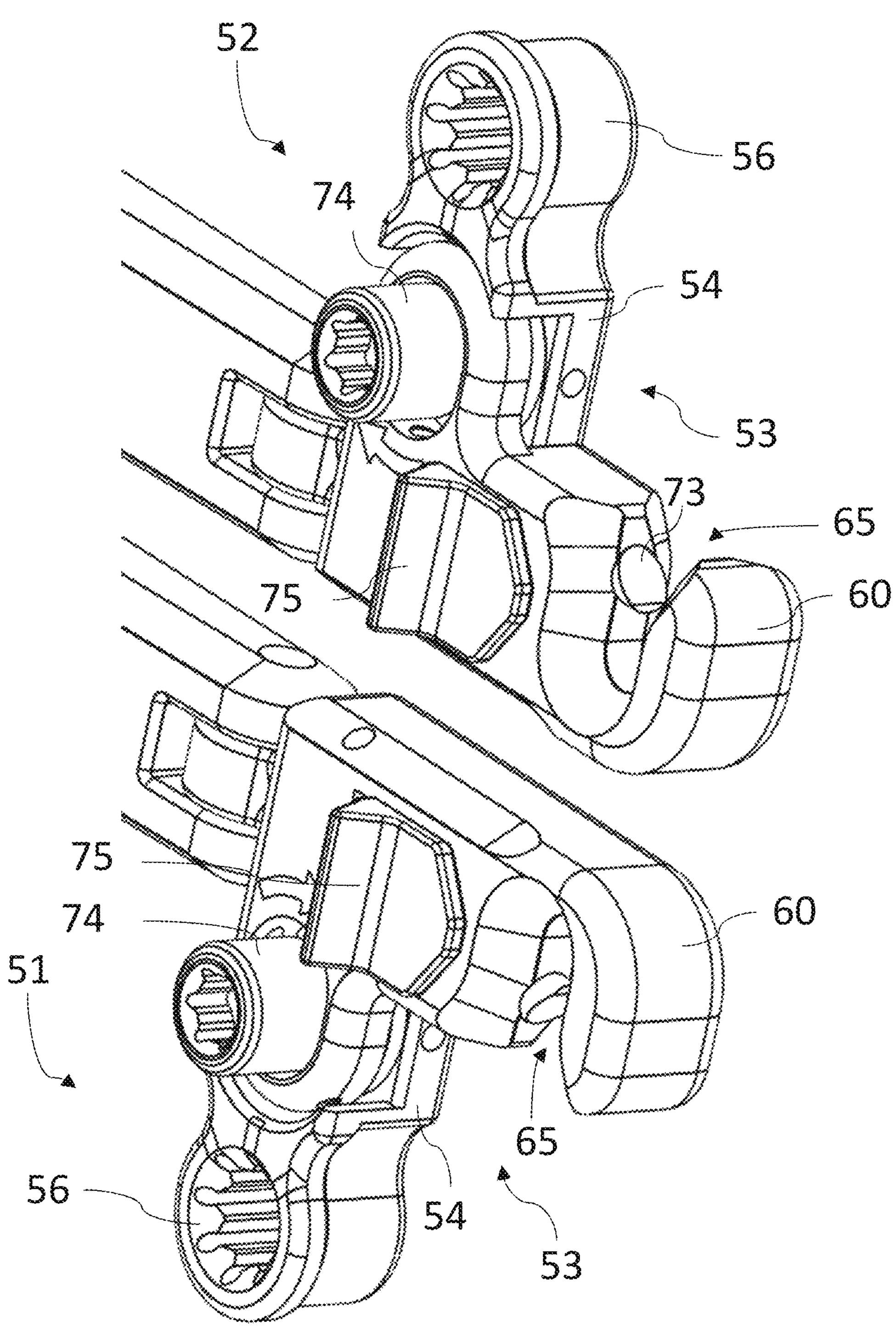
FIG. 5 illustrates a close-up perspective view of a distal end of the retractor of FIG. 1, specifically illustrating blade engagements at the distal end.
Figure 6:
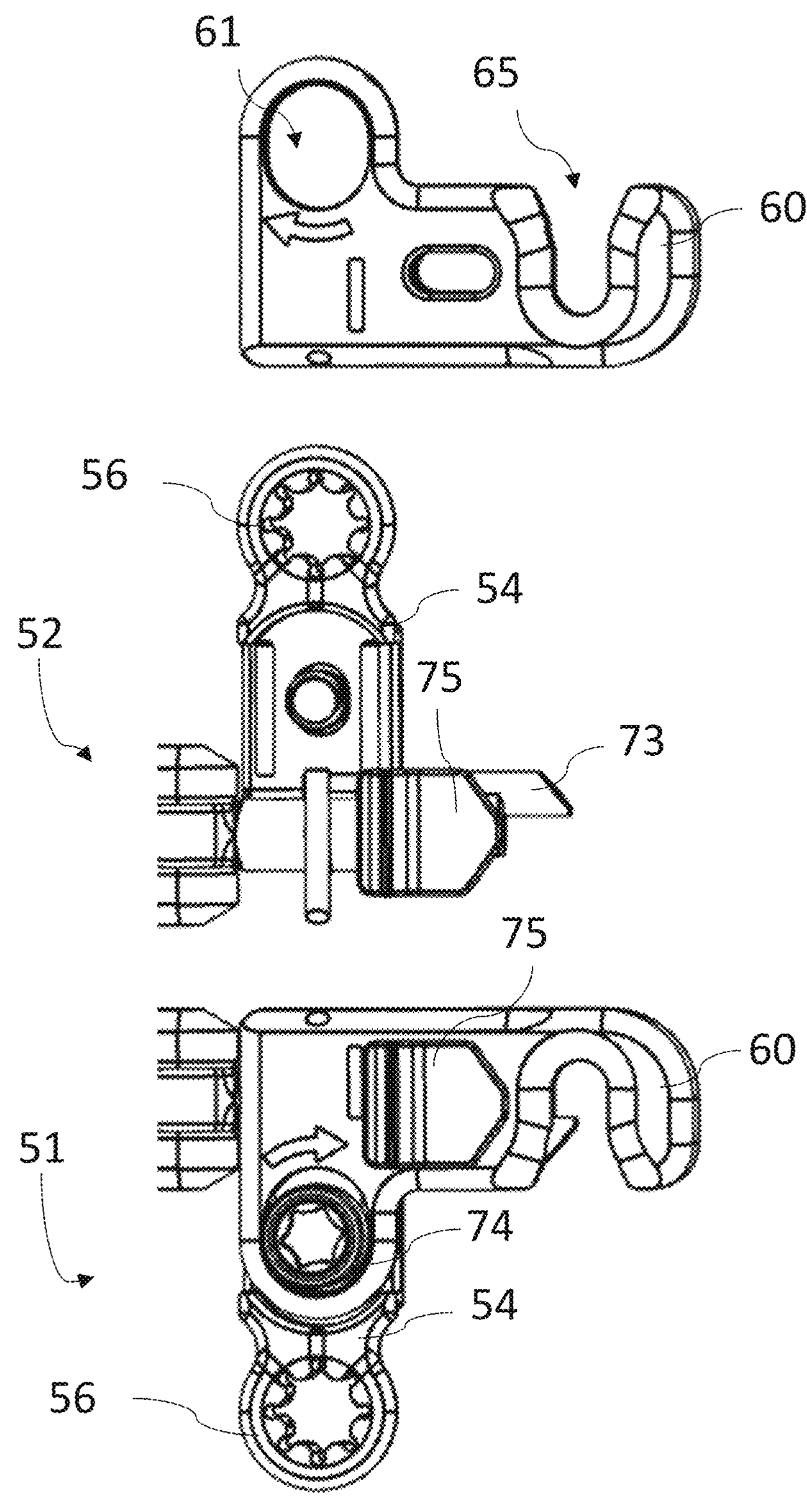
FIG. 6 illustrates a partially exploded view of the distal end of the retractor of FIG. 1.

FIG. 5 illustrates a close-up view and FIG. 6 illustrates a partially exploded view of the distal end 50 of the retractor 100 of FIG. 1, specifically illustrating blade engagements 51, 52 at the distal end 50. In this configuration, the first and second blade engagements 51, 52 are substantially identical and contain the same components. As such, the reference numbers for the first blade engagement 51 will be similarly used with the second blade engagement 52.

In some embodiments, each of the first blade engagement 51 and the second blade engagement 52 include a body 53 that may be substantially L-shaped. The body 53 of the blade engagements are in connection with the proximal portion 10 of the retractor 100 via an arm (31 or 32). The body 53 of the blade engagements may be formed from a single or unitary piece, or in some embodiments the body 53 may be formed from two pieces such that the pieces may move relative to each other. For example, in some embodiments the body may be formed of a platform 54 and a top portion 60 that rests on and engages with the platform 54. When the top portion 60 is engaged with the platform 54, the body 53 is formed. The platform 54 may include an adaptor 56 (positioned towards the lateral sides 101, 102, respectively, of the retractor 100) for engaging or selectively connecting the retractor 100 to a table-mounted surgical arm. The top portion 60 defines a receptacle 65 for receiving a blade head of a blade 80. The receptacle 65 may correspond to a distal end of the retractor 100. In configurations where the body 53 is unitary, the body 53 includes the receptacle 65 and/or adaptor 56.

Additionally, each of the first blade engagement 51 and the second blade engagement 52 may include a latch 73 for at least partially closing the receptacle 65, a knob 74 for angularly rotating the top portion 60 relative to the platform 54 of the body 53, and a release latch 75 for selectively retracting the latch 73 and opening the receptacle 65. The release latch 75 may be mechanically connected to the latch 73 such that actuation of the release latch 75 (e.g., pulling the release latch 75 proximally) causes the latch 73 to move proximally and recess into the body 53 and open the receptacle 65.

Figure 7:
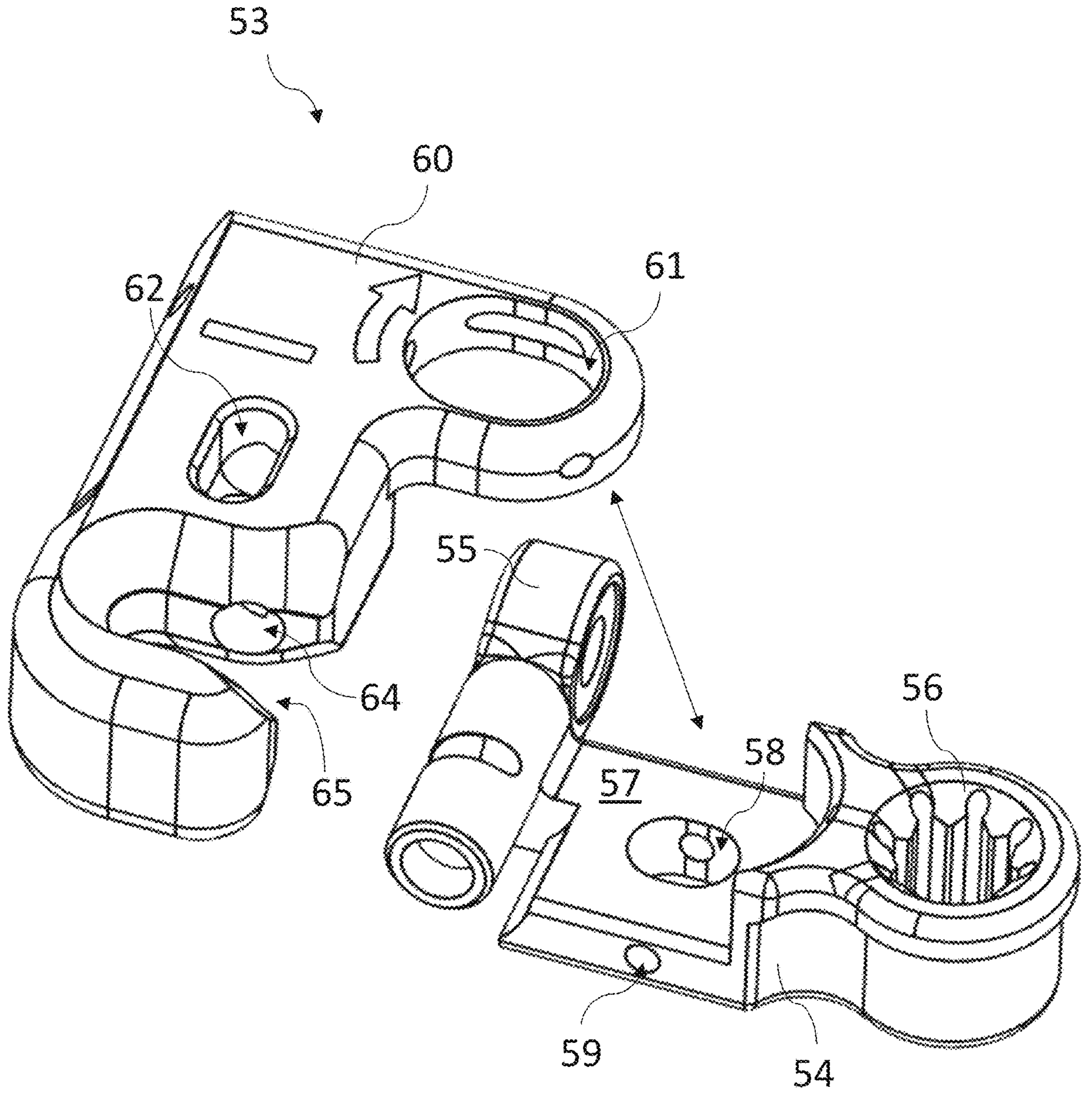
FIG. 7 illustrates an exploded view of a body of the blade engagement at the distal end of the retractor.
Figure 8:
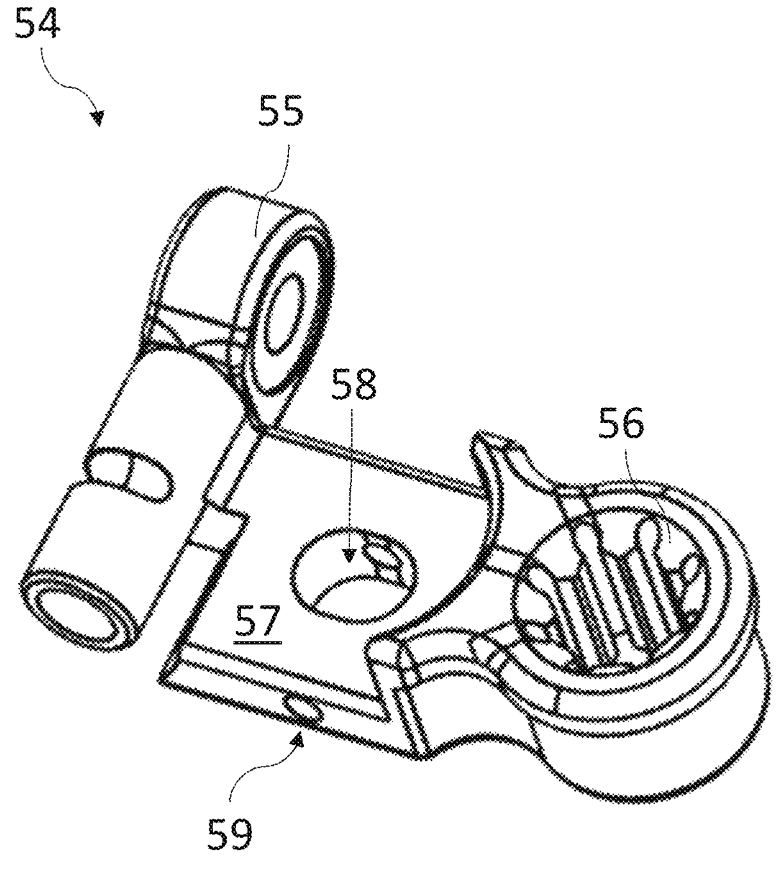
FIG. 8 illustrates a side, perspective view of a platform from the body of FIG. 7.

FIG. 7 illustrates an exploded view of the body 53 of the first and second blade engagements 51, 52 at the distal end 50 of the retractor 100. FIG. 8 illustrates the platform 54. Referring to FIGS. 7 and 8, the platform 54 may have a recess 57, recessed relative to the adaptor 56, for receiving and engaging a portion of the body 53. The platform 54 additionally includes a hinge portion 55 for connecting the body 53 to the first arm 31 or the second arm 32. For example, the hinge portion 55 may fit within a distal end 34 of a first or second arm 31, 32 (see FIG. 23) and may have a void or aperture for receiving a connection pin 35 to thereby attach the hinge portion 55 to the distal end 34 of the first or second arm 31, 32 (see FIGS. 1 to 3). A void 58 may be defined in the recess 57 and may be for pivotally receiving a screw pin 79 (see FIGS. 18A and 18B). As explained elsewhere, the knob 74 may engage with the screw pin 79 to angularly rotate or pivot the top portion 60 of the body 53 relative to the platform 54. In other configurations, the body 53 may be connected to the first arm 31 or second arm 32 through any other suitable connection means.

The top portion 60 defines a void 61 for receiving the knob 74. When the top portion 60 is positioned over the platform 54, the void 61 aligns with the void 58, allowing the knob 74 and the screw pin 79 to engage each other. The top portion 60 additionally defines a slot or channel 62 (FIG. 10A) for receiving a portion of the release latch 75. This slot or channel 62 allows the release latch 75 to be in connection with the latch 73. The receptacle 65 is defined in an opposing end of the top portion 60 from the void 61. Defined adjacent to the receptacle 65 may be a void or aperture 64 through which the latch 73 may partially extend into and over the receptacle 65.

Figure 9:
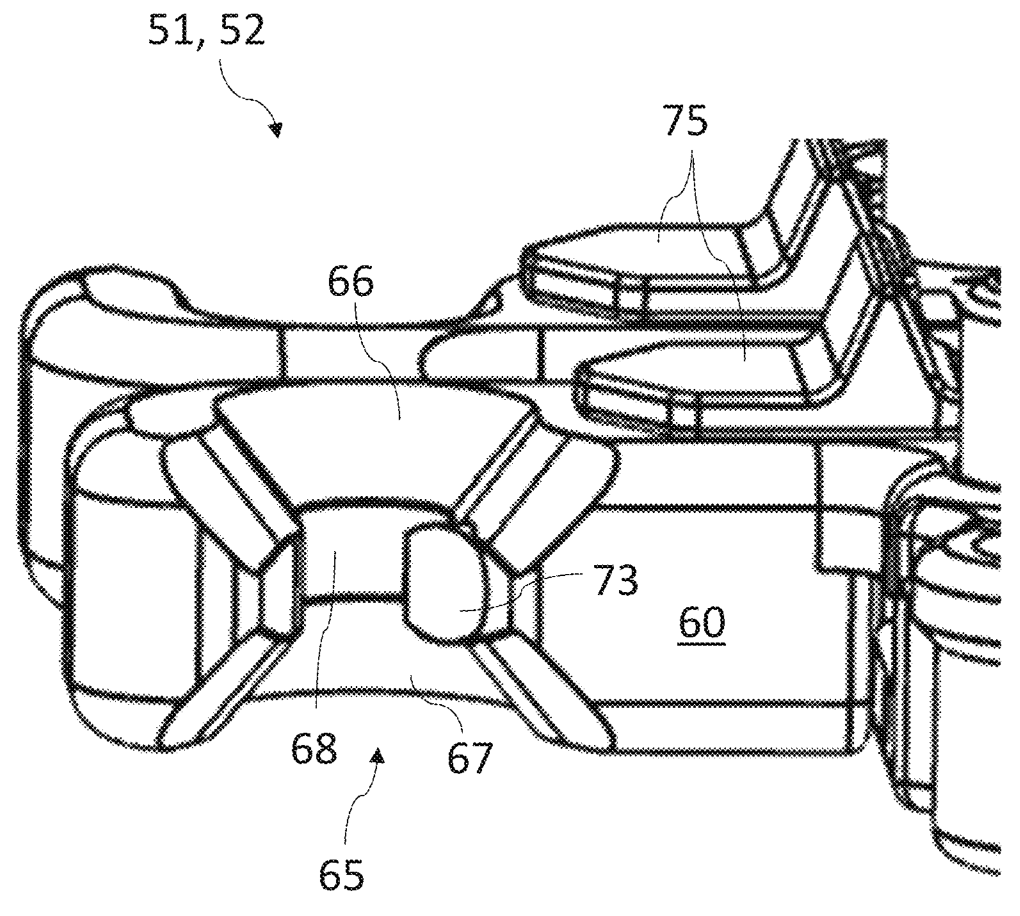
FIG. 9 illustrates a side view of the blade engagements.

FIG. 9 illustrates a side view of the blade engagements 51, 52. As illustrated, the receptacle 65 is substantially hourglass-shaped and includes a top conical portion 66 joined to a bottom conical portion 67 through a neck 68. The neck is substantially cylindrical. Other shapes for the receptacle 65 can also be used, such that the shaped receptacle is able to receive a shaped blade head. The latch 73 is also visible extending through the aperture 64 and partially extending into the receptacle 65.

Figure 10A:
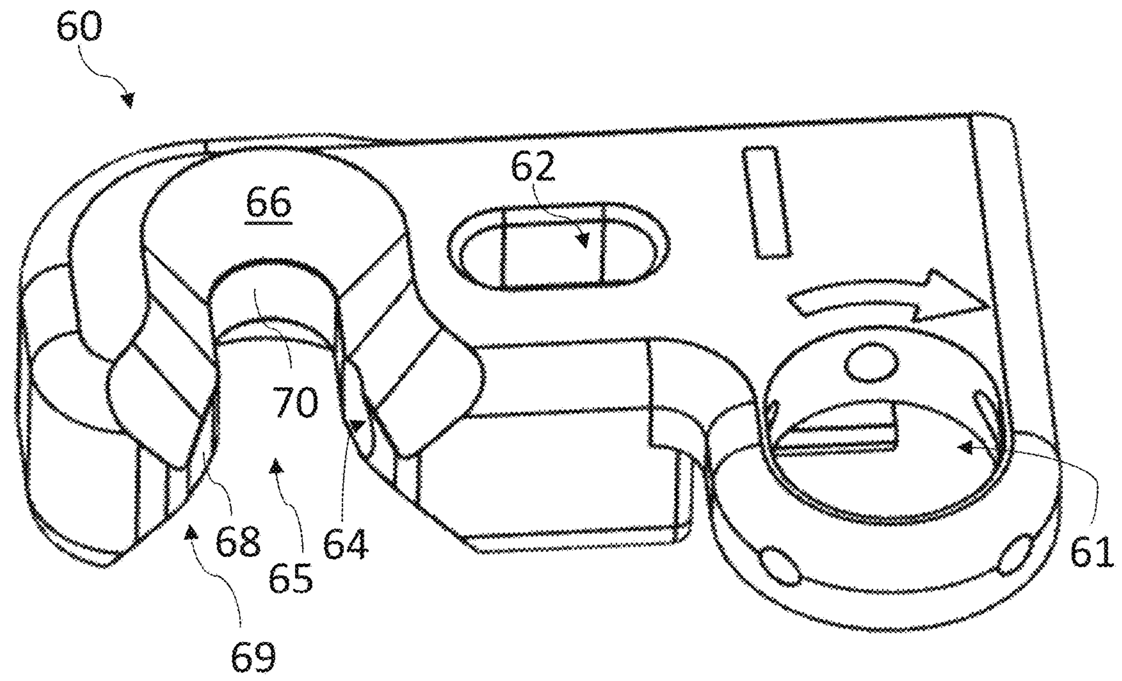
FIGS. 10A and 10B illustrate a top, side perspective view of a top portion from the body of FIG. 7.
Figure 10B:
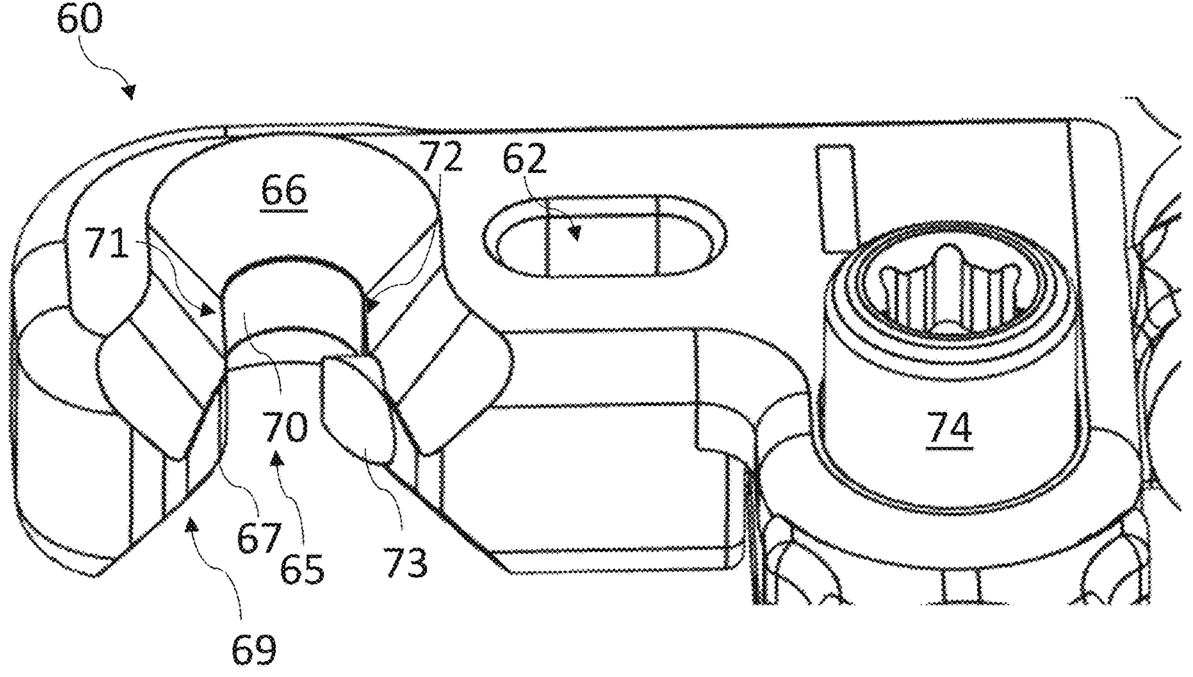
Figure 11:
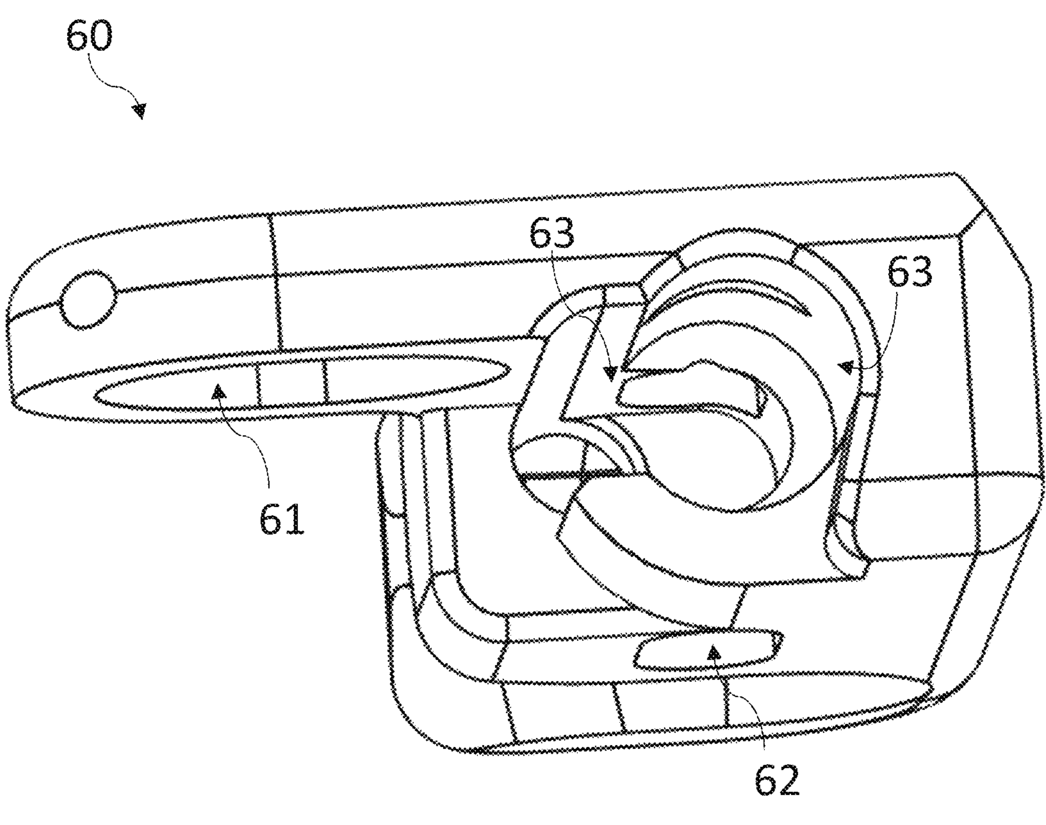
FIG. 11 illustrates a bottom, perspective view of the top portion from the body of FIG. 7.

FIGS. 10A and 10B illustrate a top, side perspective views and FIG. 11 illustrates a bottom, perspective view of the top portion 60 from the body 53 of FIG. 7. As before, the top portion 60 defines the void 61 for receiving the knob 74 (seen resting or housed within the void 61 in FIG. 10B). The top portion 60 also defines the slot 62, the aperture 64, and the receptacle 65.

The top conical portion 66 and the bottom conical portion 67 may be joined to each other through the neck 68 as a continuous structure, giving rise to the hourglass shape. The neck 68 may include or define an opening 69 that has a first width that narrows to a second width, the second width being smaller than the first width. The narrowing opening 69 may assist a surgeon in seating a shaped blade head within the seat 70. The seat 70 may form a shape in which to seat a blade head. The conical shape of the top and bottom conical portions 66, 67 prevents or reduces rotation and/or angulation of the blade head when it is seated within the seat 70 of receptacle 65.

Referring to FIG. 11, the top portion 60 of the body 53, or the body 53, also defines a channel 63 through which the latch 73 extends and which houses a portion of the release latch 75. The latch 73 may be a rod, and the channel 63 may be shaped and sized to house both the latch 73 and a portion of the release latch 75. The channel 63 may also house a spring 76 (see FIG. 14) for biasing the latch 75 towards and partially across the receptacle 65. The latch 73 may have a chamfer or angled face **73*f* that allows the blade head to slide along the latch, pushing it inwardly within the channel 63, as the blade head enters the receptacle 65. As the blade head is funneled into the receptacle 65, the blade head will slide along the chamfer of the latch 73, overcoming the spring force of the spring 76, and causing the latch 73 to depress into the channel 63. Once the blade head has been seated within the receptacle 65, the spring force of the spring 76 will cause the latch 73 to spring out of the aperture 64 to partially close the receptacle 65 and lock the blade head within the receptacle 65 to reduce translation of the blade head relative to the retractor. This action is discussed more fully with respect to FIGS. 13 through 16**.

Any suitable footprint for a blade receptacle 65 can be used. In some configurations, the neck 68 defines the opening 69 that allows a blade head or other instrument to be funneled into the receptacle 65. The neck 68 includes or defines a portion of the seat 70 against which a portion of the blade head will rest when fully seated within the receptacle 65. The neck 68 also includes a first sidewall 71 and a second sidewall 72 opposite the first sidewall 71 (see FIG. 10B). The first and second sidewalls 71, 72 may be substantially planar or flat, further reducing translation, rotation, and/or angulation of the blade head when the blade head is received within the receptacle 65. Preventing or reducing translation, rotation, and/or angulation of the blade head similarly prevents translation, rotation, and/or angulation of the blade to which the blade head is attached (e.g., blade 80 of FIGS. 1 to 4). The aperture 64 for the latch 73 may be defined within the second sidewall 72.

Figure 12:
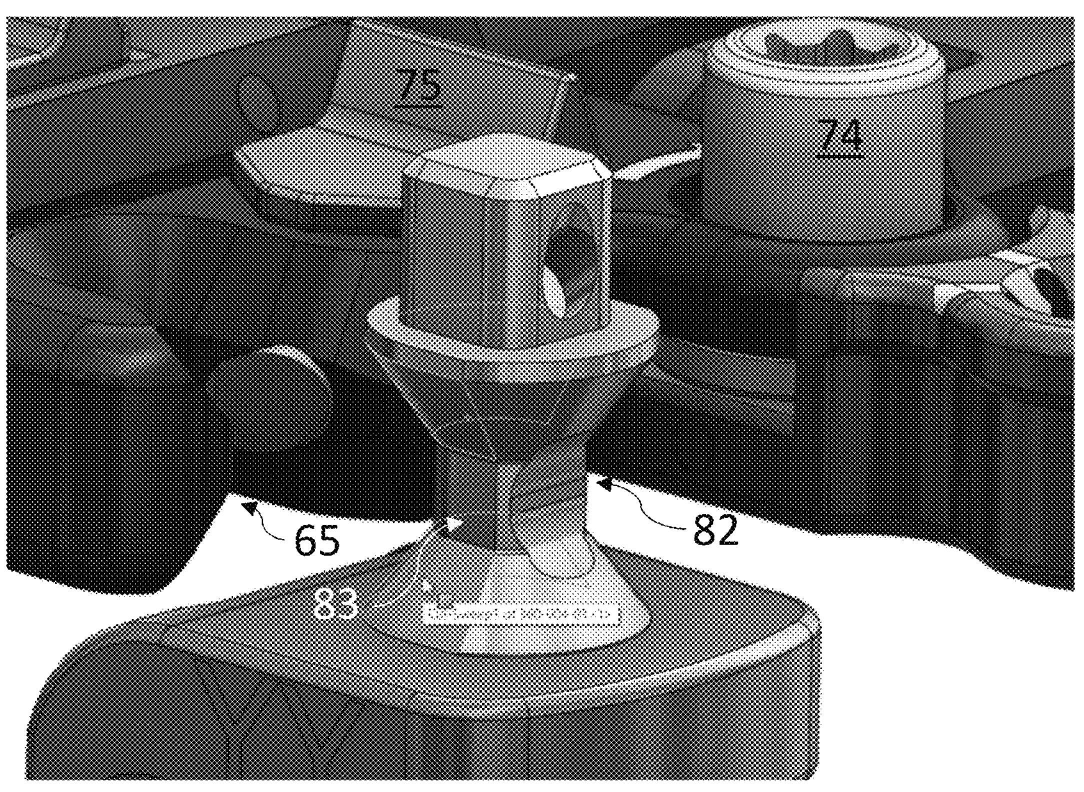
FIG. 12 illustrates a side, perspective view of the blade receptacle and a blade head to be received by the blade receptacle.
Figure 13:
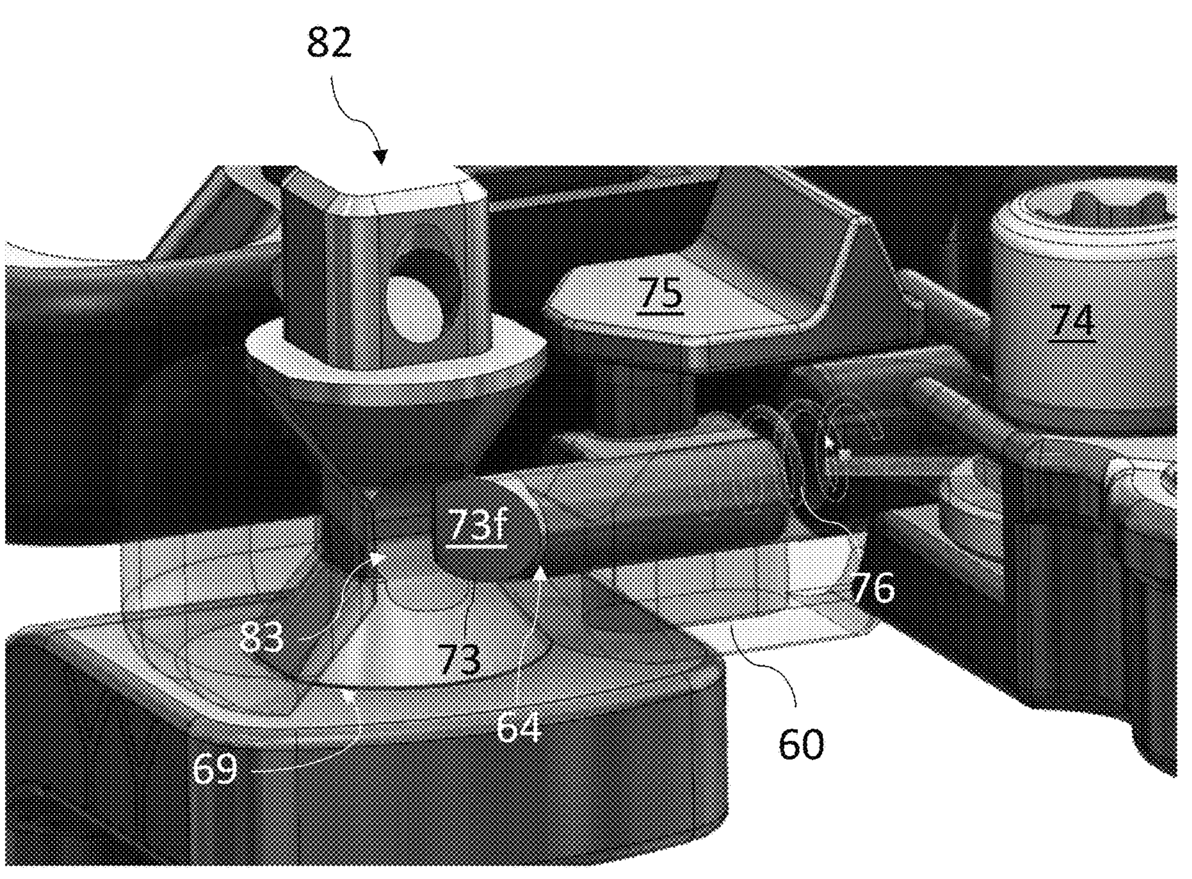
FIG. 13 illustrates the blade receptacle of FIG. 12 having received the blade head.
Figure 14:
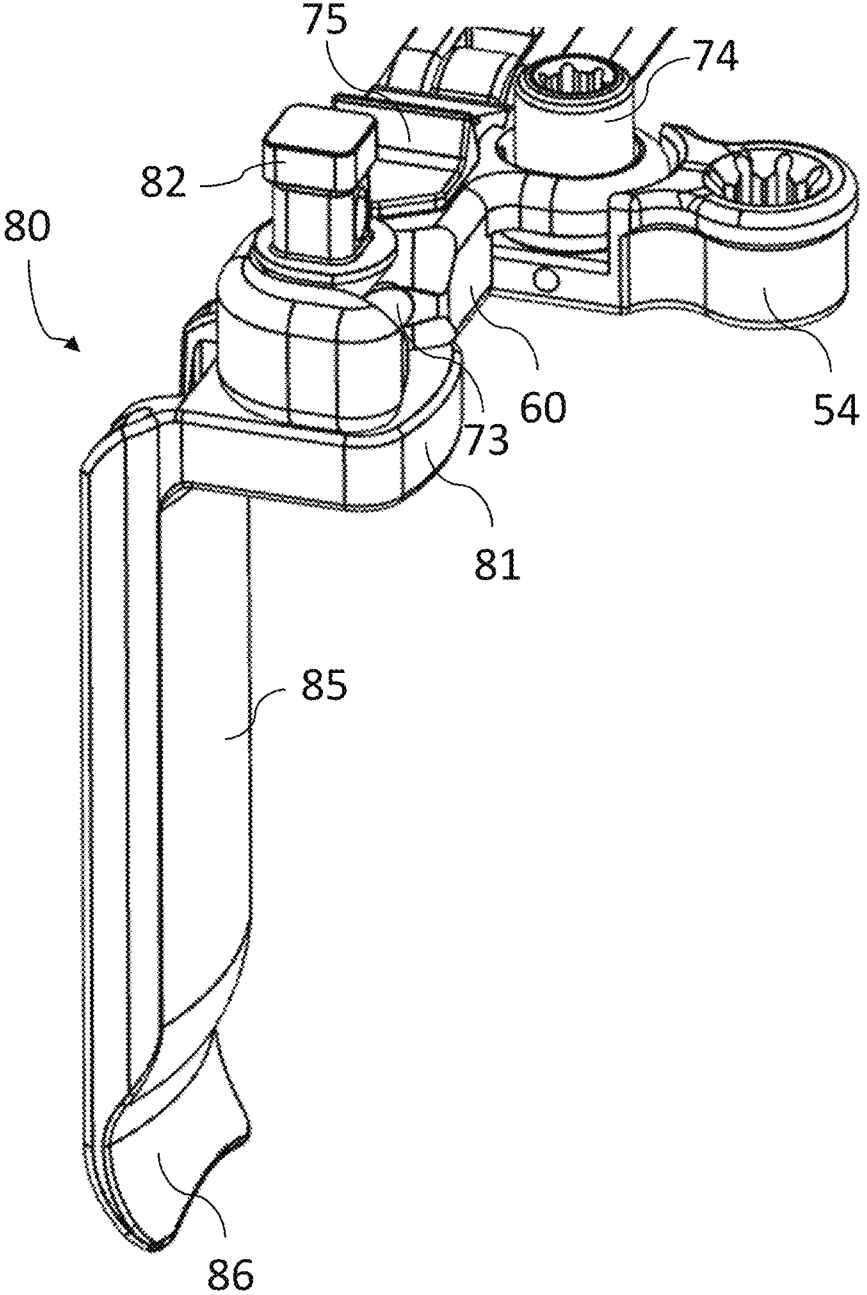
FIG. 14 illustrates another view of the blade receptacle having received the blade head.
Figure 15:
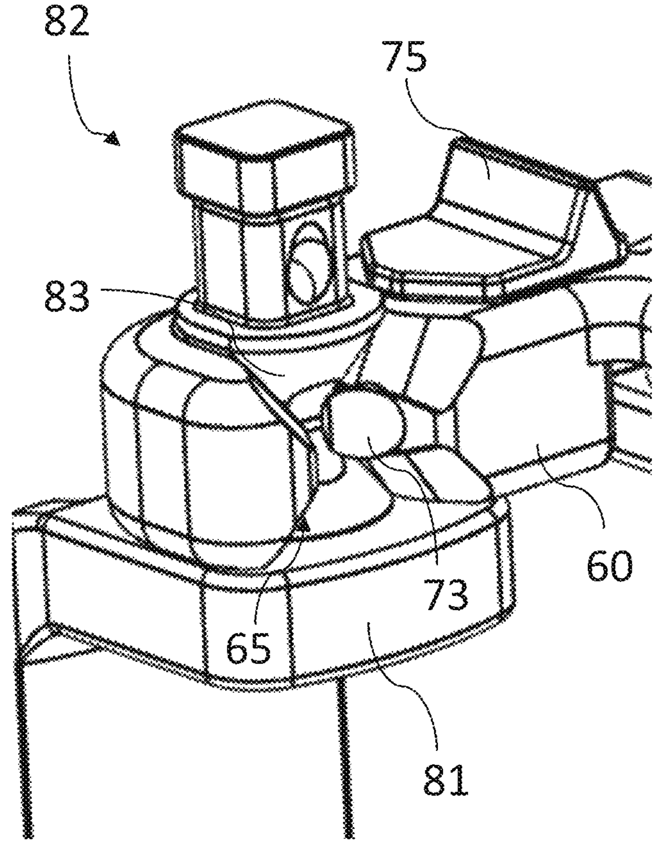
FIG. 15 illustrates a close-up view of the blade head received within the blade receptacle of FIG. 14.

FIG. 12 illustrates a side, perspective view of the blade receptacle 65 and a blade head 82 to be received by the blade receptacle 65. FIGS. 13 through 15 illustrate additional views of the blade receptacle 65 having received the blade head 82. The blade receptacle 65 may be the blade receptacle 65 of either the first blade engagement 51 or the second blade engagement 52.

As illustrated, the blade head 82 has a substantially hourglass portion 83 that corresponds to the hourglass shape of the blade receptacle 65. Therefore, when the blade head 82 is seated and positioned within the blade receptacle 65, the hourglass shape of the blade head 82 closely fits within the blade receptacle 65. For example, a planar portion of the hourglass portion 83 may align with and abut both the first sidewall 71 and the second sidewall 72 of the neck 68. Additionally, a top portion of the hourglass portion 83 may align with and abut the top conical portion 66; a bottom portion of the hourglass portion 83 may align with and abut the bottom conical portion 67.

As shown in FIG. 13, the latch 73 extends through the aperture 64 and partially across the opening 69 of the blade receptacle. A spring 76 is illustrated within the top portion 60 (e.g., within the channel 63) and biases the latch 73 towards and partially across the blade receptacle 65. Also illustrated is the face **73*f* of the latch 73, which may have a chamfer or angle allowing the blade head 82 to slide across the face 73*f* and into the receptacle 65. As the blade head 82 slides across and over the face 73*f*, the spring 76 is compressed and the latch 73 is depressed into the channel 63. When the blade head 82 is seated within the blade receptacle 65, as shown in FIG. 15, the latch 73 springs out of the aperture 64 to lock the blade head 82 within the blade receptacle 65 and further prevent or reduce rotation, translation, and/or angulation of the blade head 82**.

The blade head 82 may be positioned at a proximal end 81 of the blade 80. The blade 80 may also include a blade body 85 that extends between the proximal end 81 and a distal end 86. The blade body 85 and/or the distal end 86 may be sharp or include cutting edges, such that positioning the blade 80 out of the way in a procedure is beneficial. Specifically, by retaining and anchoring the blade head 82 within the blade receptacle 65 of the first or second blade engagements 51, 52, the blade 80 may be prevented from moving (e.g., rotating, translating, angling) undesirably within the exposure in which the retractor 100 is placed. The blade 80 may also be held in place within the exposure, allowing the practitioner to work around the blade 80 without harming patient anatomy.

In some configurations, the exposure can be further adjusted by angular adjustment of the blade heads with respect to the retractor. As explained with respect to FIGS. 17 through 18B, the knob 74 may allow the top portion 60 of the body 53, and thus the blade receptacle 65, to angularly rotate with respect to a longitudinal axis of the first and/or second arms 31, 32. Angling the top portion 60 and thus the blade receptacle 65 also angles the blade head 82 and, thus, the blade body 85 and the distal tip 86. In this way, the blade 80 can be maneuvered out of the way of a practitioner working in the exposure.

Figure 16:
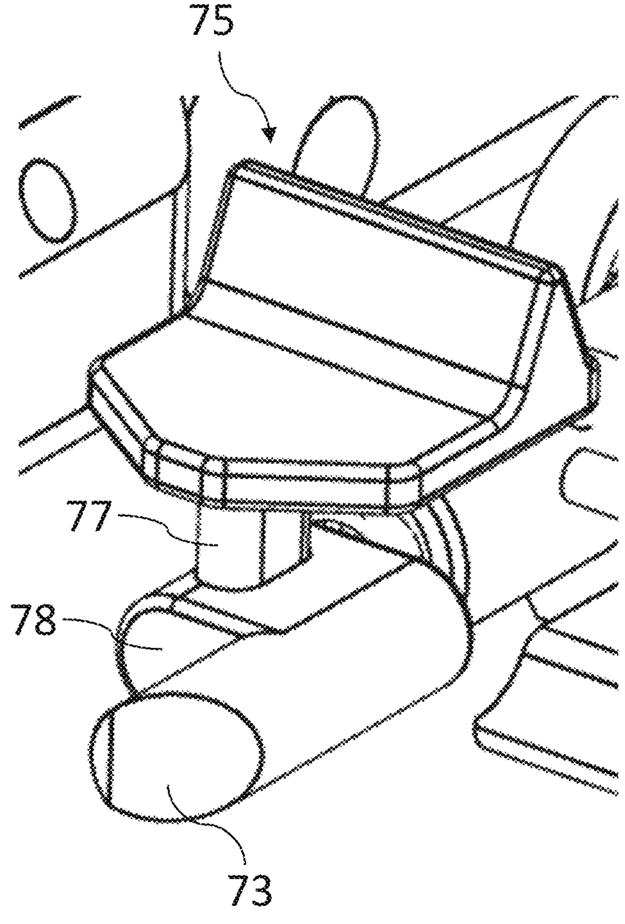
FIG. 16 illustrates a release latch for selectively opening the blade receptacle to remove the blade head.

FIG. 16 illustrates the release latch 75 for selectively opening the blade receptacle 65 to remove the blade head 82 and the blade 80, when appropriate. The release latch 75 includes a base portion 77 that is in connection with a base portion 78 of the latch 73. Upon actuation of the release latch 75, the base portion 77 of the release latch 75 and the base portion 78 of the latch 73 will be recessed into the channel 63, allowing the blade receptacle 65 to be opened.

Figure 17:
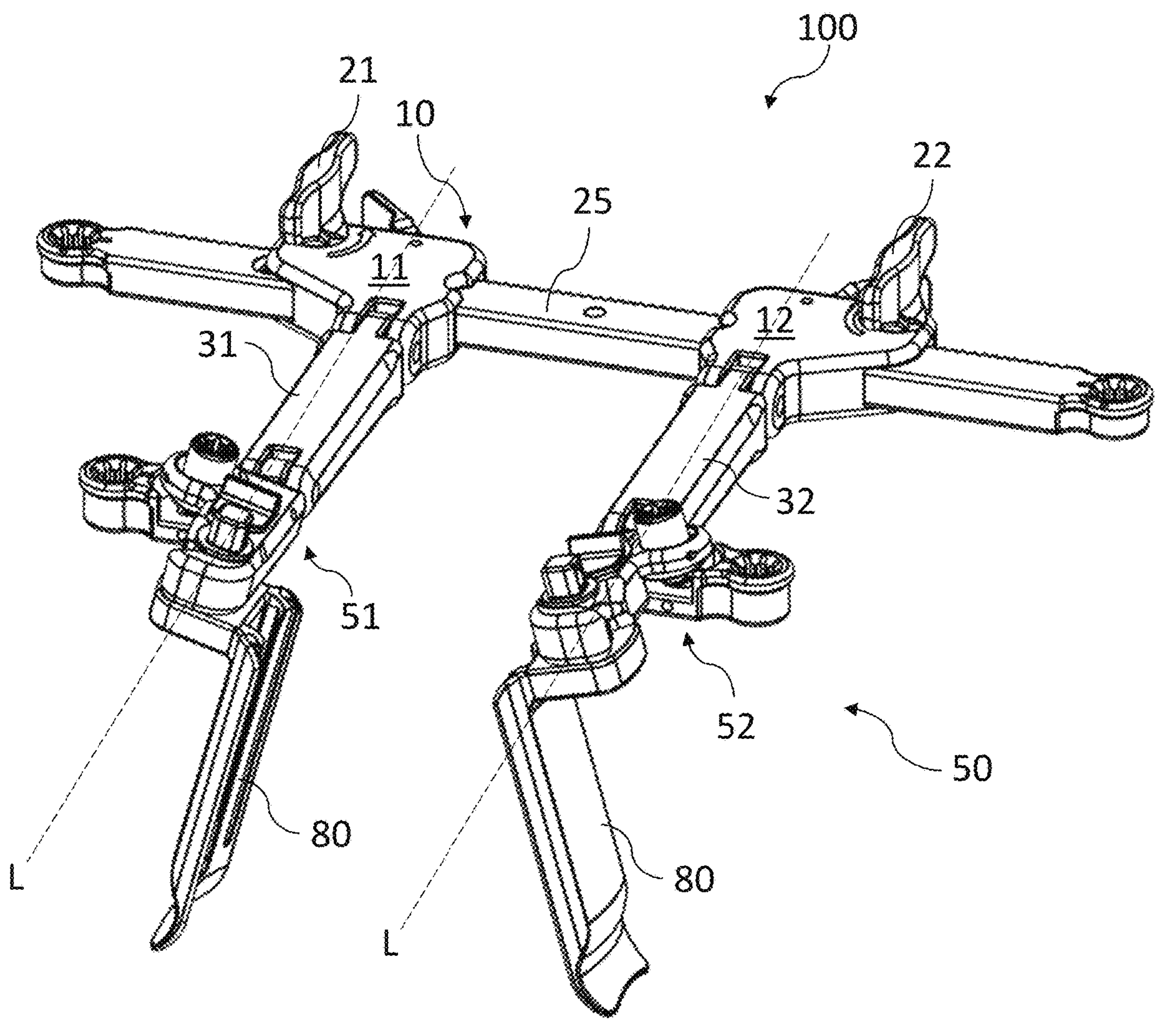
FIG. 17 illustrates the retractor of FIG. 1 where each blade receptacle has received a blade head, the retractor is in an expanded position, and the blade engagements have been angularly rotated.
Figure 18A:
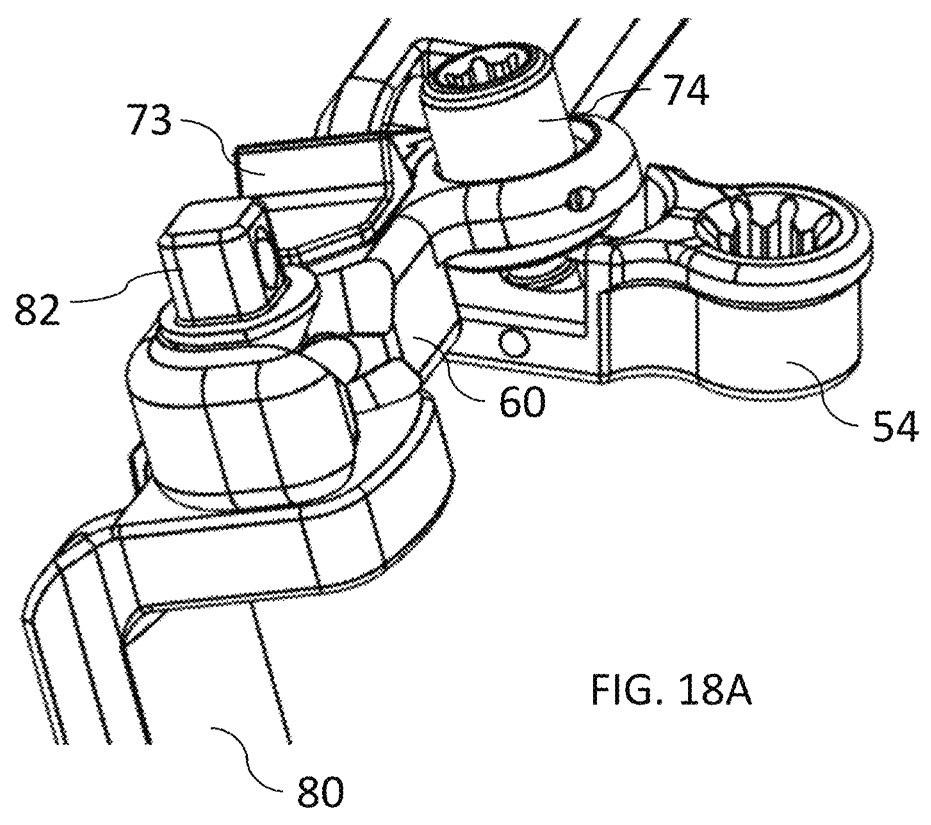
FIG. 18A illustrates a close-up view of one of the blade engagements from FIG. 17 that has been angularly rotated and FIG. 18B illustrates a cross-sectional view of a portion of the angularly rotated blade engagement.
Figure 18B:
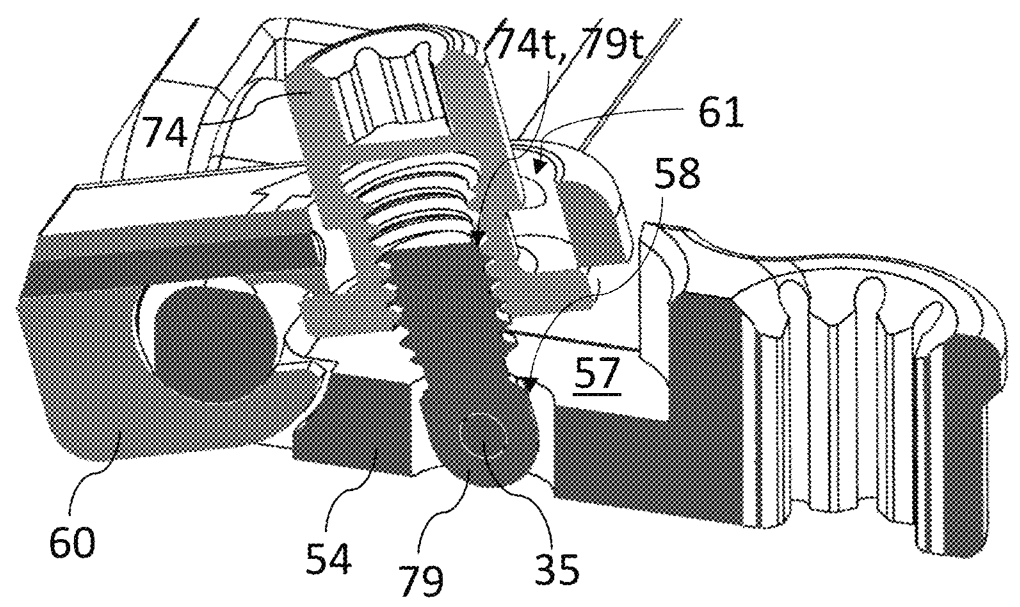

FIG. 17 illustrates the retractor 100 of FIG. 1 where each blade engagement 51, 52 have each received a blade head, the retractor 100 is in an expanded position, and the blade engagements 51, 52 have been angularly rotated. FIG. 18A illustrates a close-up view of one of the blade engagements 51, 52 from FIG. 18 that has been angularly rotated and FIG. 18B illustrates a cross-sectional view of a portion of the angularly rotated blade engagement 51, 52.

As described, the top portion 60 defines the void 61 for receiving the knob 74. The knob 74 is mechanically connected to the screw pin 79, which is positioned within the void 58 defined in the platform 54. Specifically, the knob 74 may include internal threads 74*t* that mate with threads 79*t* of the screw pin 79. The screw pin 79 may be positioned within the void 58 and secured by a connection pin 35 that extends through apertures 59 that are defined within the platform 54 transverse to the void 58. The connection pin 35 extending between and through the apertures 59 allows the screw pin 79 to rotate or pivot about the connection pin 35.

When the knob 74 is actuated, such as by rotating the knob 74 (in some configurations, a tool with a head that mates within a void of the knob 74 can be provided), the screw pin 79 is moved along with the knob 74. Specifically, the threads 74*t* of the knob 74 are engaged with the threads 79*t* of the screw pin 79, which cause the screw pin 79 to move relative to the knob 74, pivoting about the connection pin 35. Once lifted, the knob 74 may be further actuated or angled, causing the top portion 60 to be angled. For example, as shown in FIG. 17, the top portion 60 may be angled relative to a longitudinal axis L of the first arm 31 or the second arm 32. Angling the top portion 60, with the retained blade head 82, also angles the blade 80 relative to the longitudinal axis L of the first or second arms 31, 32. In this way, the blade 80 can be safely positioned out of the way within the exposure.

Figure 19:
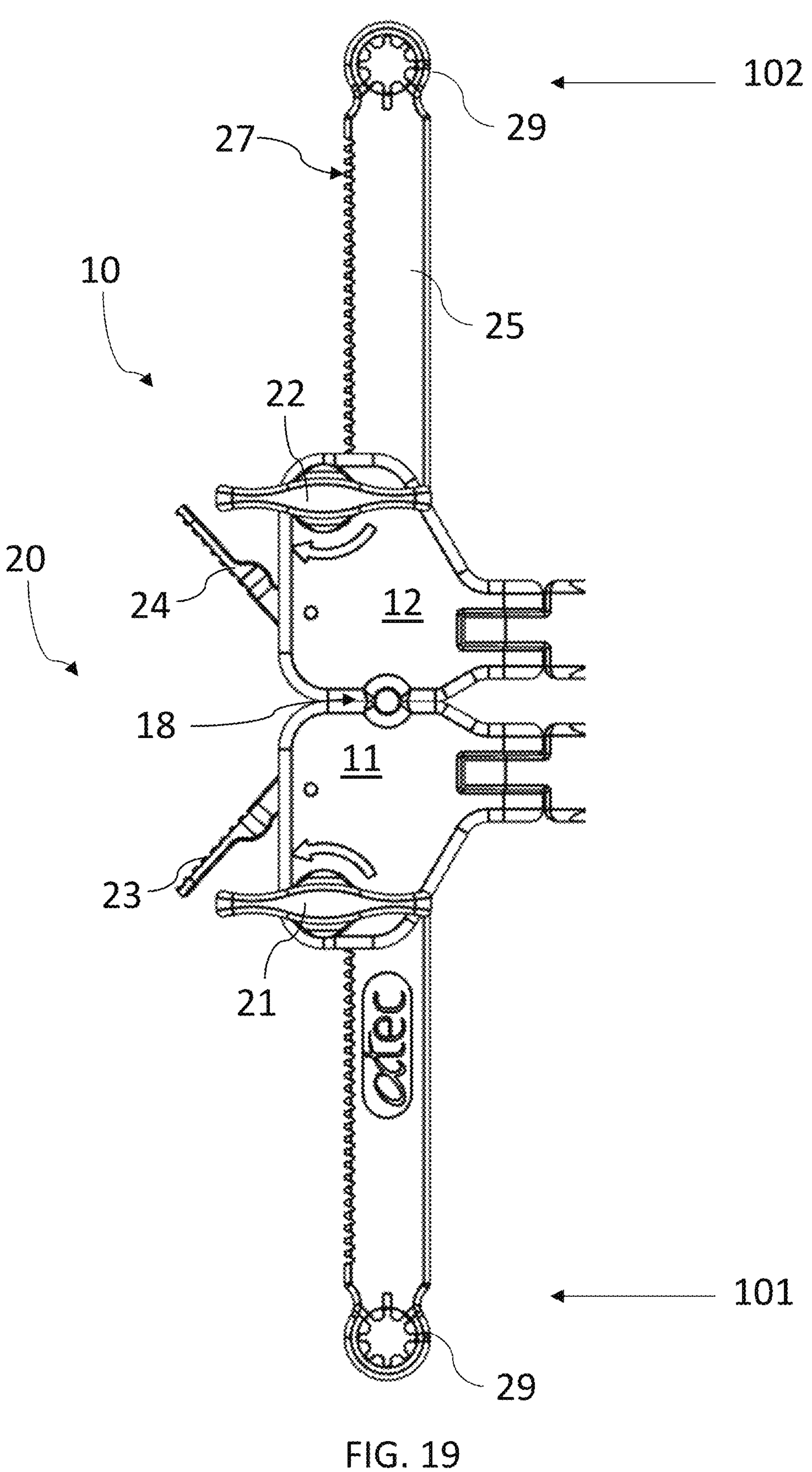
FIG. 19 illustrates a top view of a proximal portion of the retractor of FIG. 1.
Figure 20:
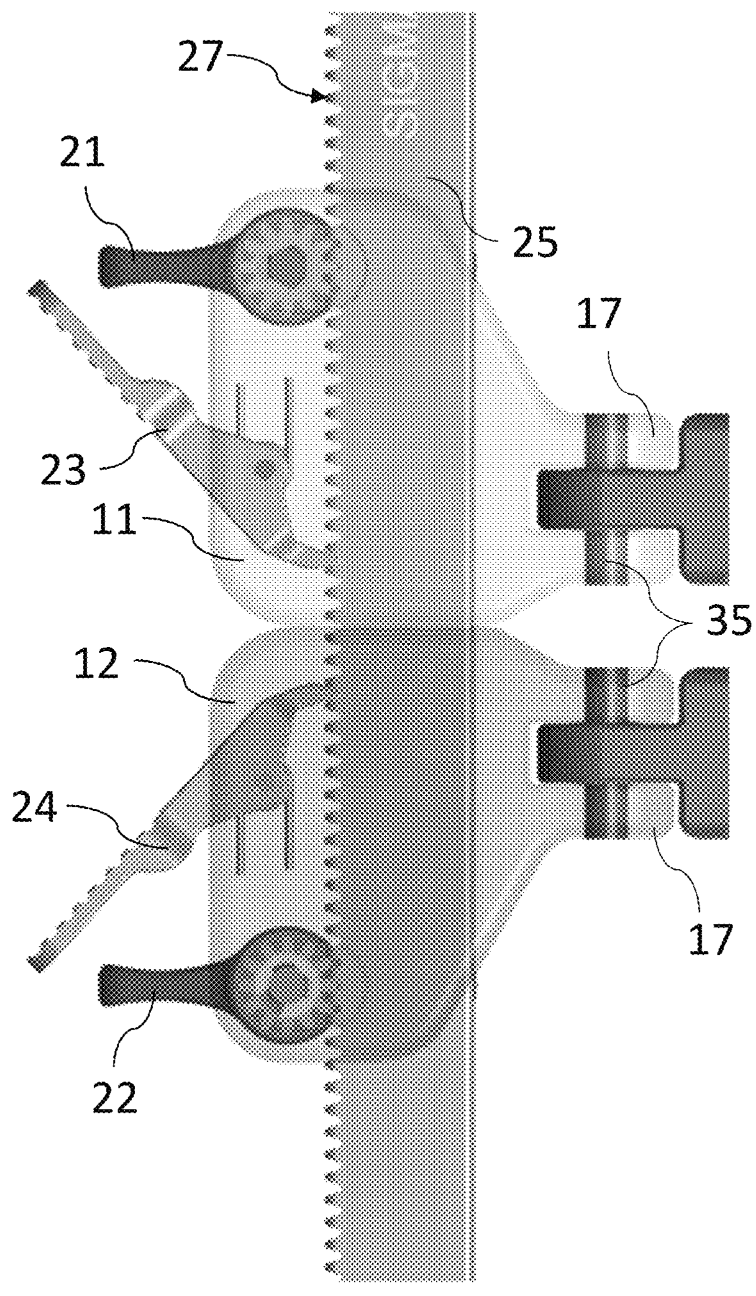
FIG. 20 illustrates a rear view of the proximal portion of FIG. 19, where the first and second cabins are transparent.
Figure 21:
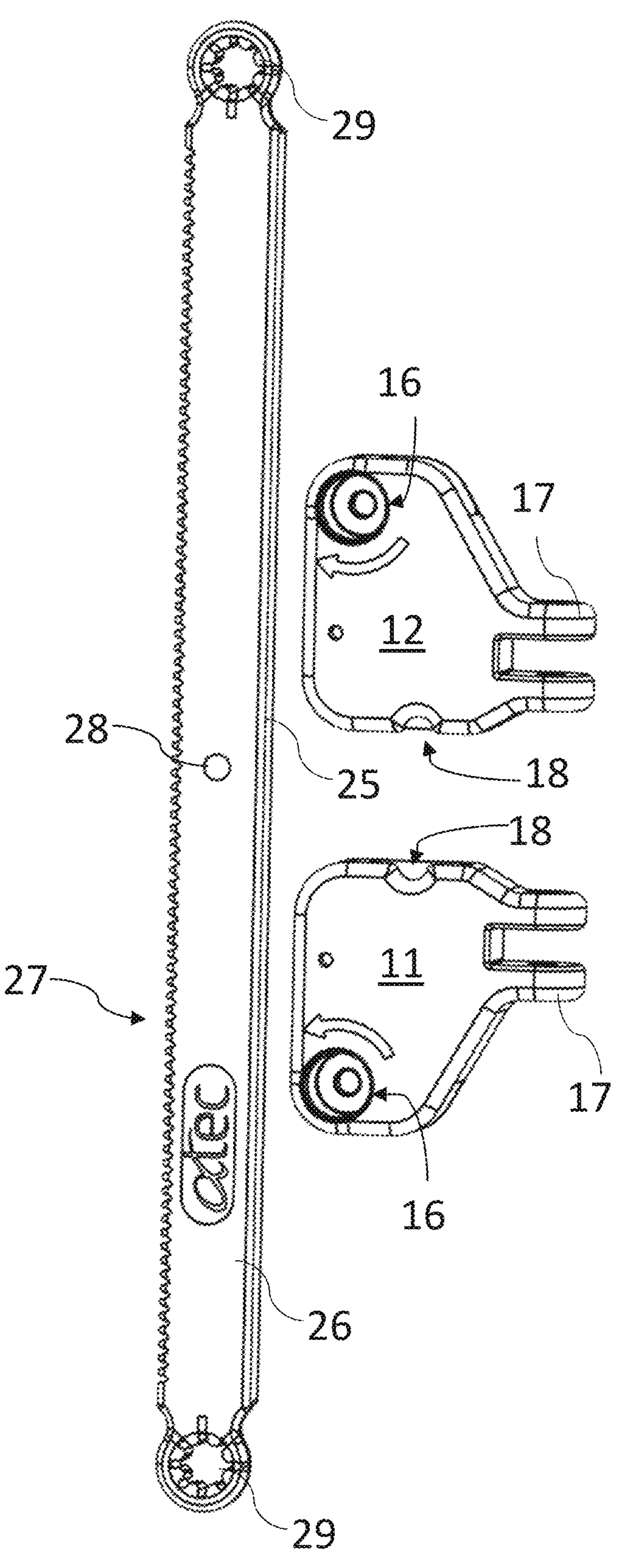
FIG. 21 illustrates a partially exploded view of the proximal portion of FIG. 19.

With reference now to the FIGS. 19-22, the proximal portion of the retractor with the rack and pinion is shown. FIG. 19 illustrates a top view, FIG. 20 illustrates a back view, and FIG. 21 illustrates a partially exploded view of the proximal portion 10 of the retractor of FIG. 1. The proximal portion 10 includes the first cabin 11, the second cabin 12, and the rack-and-pinion mechanism 20. The rack-and-pinion mechanism 20 includes the rack 25, a first pinion 21 in connection with the first cabin 11, and a second pinion 22 in connection with the second cabin 12. The proximal portion 10 also includes a first pawl 23 in connection with the first cabin 11 and a second pawl 24 in connection with the second cabin 12.

The rack 25 includes a body 26 having teeth 27 extending between the adaptors 29 at either end of the body 26. The body 26 of the rack 25 extends through the first and second cabins 11, 12, such that the first and second pinions 21, 22 may engage the teeth 27 of the rack 25. Specifically, the first and second pinions 21, 22 are gears that engage the teeth 27 and allow the first or second cabins 11, 12 to be retracted or moved along the rack 25. Generally, the first and second cabins 11, 12 are retracted along the rack 25 in opposite directions from each other (e.g., the first cabin 11 is retracted towards the first lateral side 101 and the second cabin 12 is retracted towards the second lateral side 102).

The first and second pawls 23, 24 maintain a position or location of the first and second cabins 11, 12, respectively, along the rack 25, and bias movement in an outward direction (i.e., the first cabin 11 towards the first lateral side 101 and the second cabin 12 towards the second lateral side 102). Specifically, as seen in FIG. 20, the first and second pawls 23, 24 engage teeth of the rack 25. As the cabins 11, 12 are retracted along the rack 25 through actuation of the pinions 21, 22, respectively, the pawls 23, 24 will retract along the rack 25 with the movement of the cabins 11, 12. When the cabins 11, 12 are in a desired location upon the rack 25, the pawls 23, 24 engage teeth 27 of the rack 25 at the desired location. Engagement of the teeth 27 by the pawls 23, 24 prevents "backward" or "inward" motion of the cabins 11, 12.

Specifically, engagement of the teeth 27 by the pawls 23, 24 prevents the cabins 11, 12 from moving back towards the center or medial line 103 and prevents movement of the cabins 11, 12 towards each other. Thus, the pawls 23, 24 ensure that, once the cabins 11, 12 have been retracted along the rack 25 to a desired location or desired expansion of the retractor 100 (see FIGS. 3 to 4 and FIG. 18), the cabins 11, 12 stay in the desired location and the retractor 100 stays expanded. If a user desires to move the retractor from the expanded position back to a zeroed position, the pawls must be actuated or lifted away from the teeth to allow the inward movement of the cabins.

Figure 22A:
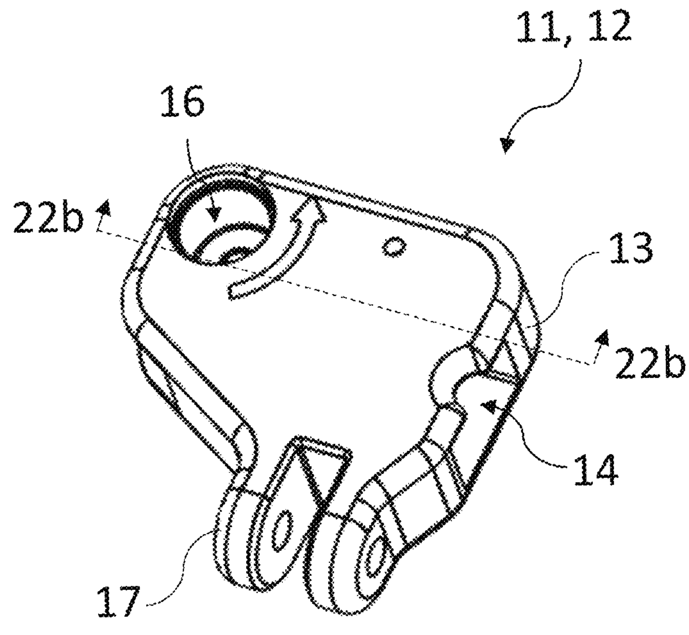
FIG. 22A illustrates a top, perspective view of a cabin from the proximal portion of FIG. 21
Figure 22B:
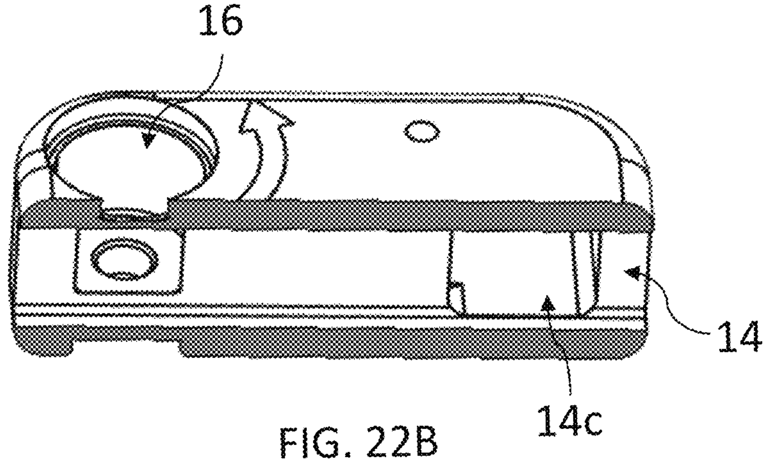
FIG. 22B illustrates a cross-sectional view of the cabin.

FIG. 22A illustrates a top, perspective view of a cabin 11, 12 from the proximal portion 10 of FIG. 20 and FIG. 22B illustrates a cross-sectional view of the cabin 11, 12 taken along line 22B of FIG. 22A. Similar to the first and second blade receptacles 51, 52, the cabins 11, 12 are substantially identical and mirror images of each other, thus like reference numerals will be used to describe the cabins 11, 12.

Each of the first and second cabins 11, 12 includes a medial edge 13 that is oriented towards the center or medial line 103 of the retractors. The cabins 11, 12 define a void 16 for receiving the pinions 21, 22 and allowing the pinions 21, 22 to engage with the rack 25 through the cabins 11, 12. The void 16 may defined in a portion of the cabins 11, 12 opposite the medial edge 13. The cabins 11, 12 additionally define a first channel 14 for receiving the body 26 of the rack 25 and a second channel 14*c* for receiving the pawls 23, 24. That is, the pawls 23, 24 are placed in mechanical connection with the teeth 27 of the rack 25 and the cabins 11, 12 when the pawls 23, 24 are received within the second channels 14*c*. The void 16 for receiving the pinions 21, 22 similarly extends into the first channel 14 to allow the pinions 21, 22 to access and engage the teeth 27 of the rack 25.

Referring to FIGS. 21 to 22B together, defined in the medial edge 13 of each cabin 11, 12 is a cut-out 18, which provides a zero-position or home-position indicator for the cabins 11, 12, the rack 25, and the retractor 100. Specifically, when the cabins 11, 12 are positioned adjacent to each other (i.e., when the medial edges 13 of the cabins 11, 12 abut each other as in FIG. 19), the cut-outs 18 form a window through which a zero-position or home-position indicator 28 on the rack 25 can be seen (see FIG. 21). This provides practitioners using the retractor 25 a quick visual indication of whether the retractor 100 is in the zero- or home-position. If the zero-position or home-position indicator 28 on the rack 25 is not visible, the practitioner can adjust the placement or position of the cabins 11, 12 along the rack 25 until the zero-position or home-position indicator 28 is visible and can start a procedure with the retractor 100 in the zero- or home-position.

Figure 23:
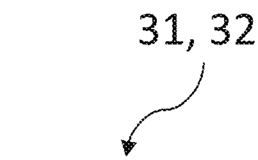
FIG. 23 illustrates an arm for connecting the proximal portion to the distal portion of the retractor of FIG. 1.
Figure 23:
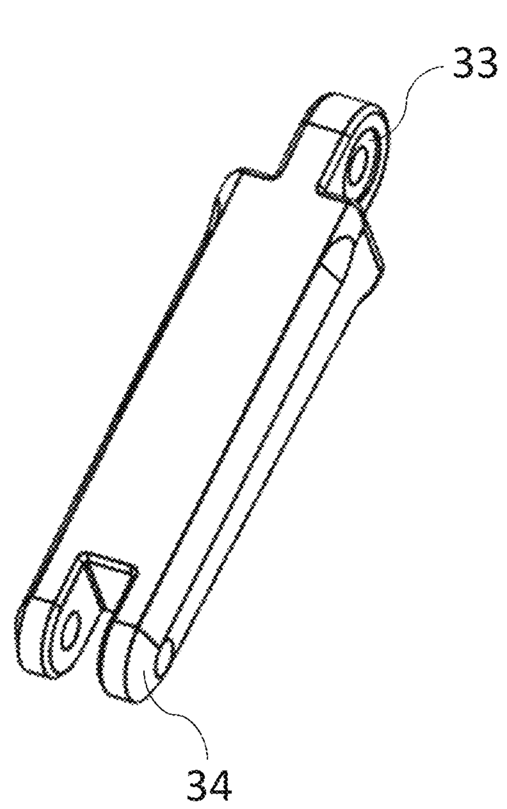

Each cabin 11, 12 includes a distal end 17, which may be an open distal end 17 for receiving a proximal end 33 of an arm 31, 32. As illustrated in FIG. 23, each arm 31, 32 includes a proximal end 33, which may include a hinge mechanism, and a distal end 34 opposite the proximal end 33. The proximal end 33 engages with the distal end 17 of the cabins 11, 12 and may be connected to the distal ends 17 of the cabins 11, 12 through a connection pin 35. The connection pin 35 allows the cabins 11, 12 and/or the proximal ends 33 of the arms 31, 32 to pivot about the connection pin 35. In this way, the entire proximal portion 10 is hingedly connected to the first arm 31 and the second arm 32.

Likewise, each distal end 34 of the arms 31, 32 is connected to the body 53 through the hinge portion 55 of platform 54 (see FIGS. 5 to 6 and FIG. 8). A connection pin 35 secures the hinge portion 55 within the distal end 34 of each arm 31, 32 and allows the hinge portion 55 to pivot about the connection pin 35. As the platform 54 having the hinge portion 55 is connected and engaged with the top portion 60, when the hinge portion 55 pivots about the connection pin 35, both the platform 54 and the top portion 60 likewise pivot about the connection pin 35. In this way, the entire distal portion 50 is hingedly connected to the first arm 31 and the second arm 32. Accordingly, the distal portion 50 may be laterally offset from the proximal portion 10, which allows the retractor 100 to be accommodated for a wide variety of patient anatomies and/or to allow a user to position the retractor 100 in any number of desired positions relative to the surgical site. In other configurations, the arms may be connected as desired to the proximal and distal portions of the retractor.

FIG. 24 is a flowchart of one example method of using or assembling the retractor of FIG. 1 with a blade. For example, the retractor 100 may be used in a surgical procedure to hold open an exposure (e.g., the workspace of the practitioner), such as an exposure in a cervical spinal procedure. The method 300 may include positioning a distal end of the retractor over an exposure, such as a cervical spine exposure, the retractor having a receptacle and a latch biased towards an opening of the receptacle, at 305. The method 300 may also include positioning a blade head of the blade that is already positioned within the exposure into the receptacle of the retractor through the opening of the receptacle, the blade head depressing the latch as the blade head is funneled into the receptacle, at 310. The method 300 may further include seating the blade head within the receptacle, at 315, and locking the blade head in place within the receptacle, reducing translation, rotation, and angulation of the blade head relative to the retractor, at 320.

Positioning the blade head into the receptacle may include sliding the blade head over a chamfer of the latch, thereby depressing the latch into a channel. Seating the blade head within the receptacle may include aligning a top conical portion of the blade head with a top conical portion of the receptacle, aligning a bottom conical portion of the blade head with a bottom conical portion of the receptacle, and aligning planar side walls of the blade head with a cylindrical/planar portion of the receptacle. The top conical portion, the cylindrical neck portion, and the bottom conical portion of the receptacle may reduce or prevent rotation and/or angulation of the blade head relative to the retractor.

Translation of the blade head may be prevented and/or reduced by locking the blade head in place within the receptacle, which may include releasing the latch from a depressed position within a channel to a biased position over a portion of the opening of the receptacle, such that a portion of the latch overlaps with a notch in the blade head, thereby preventing movement of the blade head within the receptacle. In other words, locking the blade head in place within the receptacle may include allowing the latch to return to its biased or "locked" position to cover at least a portion of the opening of the receptacle. Reducing translation, rotation, and/or angulation of the blades may also reduce post-surgical inflammation, and/or dysphagia in cervical spine procedures.

In some embodiments, the method 300 further includes angling the receptacle such that a distal tip of a blade having the blade head is angled away from the exposure and anchoring the retractor to a surgical table through one or more adaptors. Additionally, the method 300 may further include removing the retractor with the blade head locked into the receptacle from the exposure and actuating a release latch of the retractor to release the blade head from the receptacle.

As the retractor 100 may be used in a cervical spinal procedure, the retractor 100 may be sized accordingly to fit within the small space provided by a cervical spine exposure.

EMBODIMENTS

Embodiment 1: A retractor comprising:

- a proximal portion having a rack and pinion mechanism in connection with a first cabin and a second cabin such that the first and second cabins are independently retractable along the rack, the rack having a first adaptor on a first end and a second adaptor on a second end, the first and second adaptors for selectively connecting the rack to a table-mounted surgical arm;
- a distal portion opposite the proximal portion, the distal portion connected to the proximal portion through a first arm in connection with the first cabin and a second arm in connection with the second cabin,
  - the distal portion having a first blade engagement in connection with the first arm and a second blade engagement in connection with the second arm,
  - wherein the first and second blade engagements each comprise:
    - a substantially L-shaped body in connection with the first arm or second arm, respectively,
    - a receptacle defined in a first end of the L-shaped body, the receptacle having an hourglass shape for receiving a blade head,
    - a latch for covering a portion of the receptacle upon receipt of the blade head,
    - an adaptor at a second end of the L-shaped body, the adaptor for selectively connecting the distal portion to a table-mounted surgical arm,
    - a release latch for retracting the latch, and
    - an angulation knob adjacent to the adaptor at the second end of the L-shaped body, the angulation knob for rotating the L-shaped body.

Embodiment 2: The retractor of embodiment 1, wherein the hourglass shape of the receptacle prevents rotation, translation, and angulation of the blade head when the blade head is received within the receptacle.

Embodiment 3: The retractor of either one of embodiments 1 or 2, wherein the angulation knob angularly rotates the L-shaped body of the first and second blade engagements about a longitudinal axis of the first and second arms, respectively.

Embodiment 4: The retractor of any one of embodiments 1, 2, or 3, wherein the first arm is hingedly connected to the first cabin at a proximal end of the first arm and is hingedly connected to the first blade engagement at a distal end of the first arm.

Embodiment 5: The retractor of any one of embodiments 1, 2, 3, or 4, wherein the receptacle of the first blade engagement comprises a top conical portion, a bottom conical portion, and a planar cylindrical neck connecting the top conical portion to the bottom conical portion to form the hourglass shape.

Embodiment 6: The retractor of embodiment 5, wherein the neck defines an opening of the receptacle for receiving a blade head and wherein the latch extends across at least a portion of the opening when covering the receptacle.

Embodiment 7: The retractor of any one of embodiments 1, 2, 3, 4, 5, or 6, wherein the blade head comprises an hourglass shape corresponding to the hourglass shape of the receptacle.

Embodiment 8: The retractor of any one of embodiments 1, 2, 3, 4, 5, 6, or 7, wherein the rack and pinion mechanism comprises:

a first pinion for retracting the first cabin along the rack;

a first pawl for securing a position of the first cabin along the rack;

a second pinion for retracting the second cabin along the rack; and a second pawl for securing a position of the second cabin along the rack.

Embodiment 9: The retractor of embodiment 8, wherein the first and second pawls prevent inward motion of the first and second cabins, respectively, without actuating the first and second pawl.

Embodiment 10: The retractor of any one of embodiments 1, 2, 3, 4, 5, 6, 7, 8, or 9, wherein the retractor comprises a zero- or home-position indicator for determining a home or zero position of the retractor.

Embodiment 11: The retractor of any one of embodiments 1, 2, 3, 4, 5, 6, 7, 8, 9, or 10, wherein the rack comprises a zero-position indicator for determining a zero position of the retractor.

Embodiment 12: The retractor of any one of embodiments 1, 2, 3, 4, 5, 6, 7, 8, 9, 10, 11, wherein the latch for covering the receptacle upon receipt of the blade head comprises a spring-loaded rod housed within a channel and mechanically connected to the release latch.

Embodiment 13: The retractor of any one of embodiments 1, 2, 3, 4, 5, 6, 7, 8, 9, 10, 11, or 12, wherein the latch for closing the receptacle upon receipt of the blade head is biased towards and partially across an opening of the receptacle.

Embodiment 14: The retractor of embodiment 13, wherein the latch comprises:

a rod housed within a channel, the rod having a chamfered face over which the blade head slides as the blade head enters the receptacle; and a spring within the channel biasing the rod towards the opening of the receptacle, wherein the rod retracts into the channel as the blade head slides on the chamfered face, and wherein the rod returns to its bias position and locks the blade head within the receptacle when the blade head passes the rod and is received within the receptacle.

Embodiment 15: A retractor comprising:

a proximal portion; and a distal portion opposite the proximal portion, the distal portion comprising:

a first blade engagement having a blade receptacle defined in a first end of a body of the first blade engagement, the blade receptacle having an opening that narrows to a seat for receiving a blade head, the seat defining a shape that reduces translation, rotation, and/or angulation of the blade head, and a second blade engagement having a blade receptacle defined in a first end of a body of the second blade engagement, the blade receptacle having an opening that narrows to a seat for receiving a blade head, the seat defining a shape that reduces translation, rotation, and/or angulation of the blade head.

Embodiment 16: The retractor of embodiment 15, wherein the seat of each blade receptacle comprises an upper conical portion connected to a lower conical portion.

Embodiment 17: The retractor of embodiment 16, wherein the upper conical portion is connected to the lower conical portion via a planar and/or cylindrical portion.

Embodiment 18: The retractor of embodiment 7, wherein the planar and/or cylindrical portion at least partially defines the opening and the planar portion comprises a first flat portion, a U-shaped portion, and a second flat portion opposite the first flat portion.

Embodiment 19: The retractor of either one of embodiments 17 or 18, wherein the planar and/or cylindrical portion defines a void into which a latch may extend to at least partially close the blade receptacle of the first blade retractor upon receipt of a blade head, thereby locking the blade head within the blade receptacle and reducing translation of the blade head relative to the retractor.

Embodiment 20: The retractor of embodiment 15, wherein the seat of the second blade retractor comprises an upper conical portion, a lower conical portion connected to the upper conical portion by a planar and/or cylindrical side wall.

Embodiment 21: The retractor of embodiment 20, wherein the planar and/or cylindrical side wall at least partially defines the opening and the planar side wall comprises a first flat portion, a U-shaped portion, and a second flat portion opposite the first flat portion.

Embodiment 22: The retractor of either one of embodiments 20 or 21, wherein the side wall defines a void into which a latch may extend to at least partially close the blade receptacle of the first blade retractor upon receipt of a blade head.

Embodiment 23: The retractor of any one of embodiments 15, 16, 17, 18, 19, 20, 21, or 22, wherein the first blade retractor further comprises an adaptor defined in a second end of the body, and a knob for angularly rotating the first blade retractor.

Embodiment 24: A method of assembling a blade to a retractor, the method comprising:

positioning a distal end of the retractor over an exposure, the retractor having a receptacle and a latch biased towards an opening of the receptacle;

funneling a blade head of a retractor blade already positioned within the exposure into the receptacle of the retractor through the opening of the receptacle, the blade head depressing the latch as the blade head is funneled into the receptacle;

seating the blade head within the receptacle; and locking the blade head in place within the receptacle, reducing translation, rotation, and angulation of the blade head relative to the retractor.

Embodiment 25: The method of embodiment 24, wherein funneling the blade head into the receptacle comprises sliding the blade head over a chamfer of the latch, thereby depressing the latch into a channel.

Embodiment 26: The method of either one of embodiments 24 or 25, wherein seating the blade head within the receptacle comprises:
- aligning a top conical portion of the blade head with a top conical portion of the receptacle;
- aligning a bottom conical portion of the blade head with a bottom conical portion of the receptacle; and
- aligning planar and/or cylindrical side walls of the blade head with a planar portion of the receptacle, the top conical portion, the planar portion, and the bottom conical portion of the receptacle reducing translation, rotation, and angulation of the blade head relative to the retractor.

Embodiment 27: The method of any one of embodiments 24, 25, or 26, wherein locking the blade head in place within the receptacle comprises releasing the latch from a depressed position within a channel to a biased position over a portion of the opening of the receptacle, such that a portion of the latch overlaps with a notch in the blade head, thereby preventing movement of the blade head within the receptacle.

Embodiment 28: The method of any one of embodiments 24, 25, 26, or 27, further comprising angling the receptacle such that a distal tip of a blade having the blade head is angled away from the exposure.

Embodiment 29: The method of any one of embodiments 24, 25, 26, 27, or 28, further comprising anchoring the retractor to a surgical table through one or more adaptors.

Embodiment 30: The method of any one of embodiments 24, 25, 26, 27, 28, or 29, wherein the exposure is an exposure of a cervical spine procedure.

Embodiment 31: The method of any one of embodiments 24, 25, 26, 27, 28, 29, or 30, further comprising:
- removing the retractor with the blade head locked into the receptacle from the exposure; and
- actuating a release latch of the retractor to release the blade head from the receptacle.

Embodiment 32: The method of any one of embodiments 24, 25, 26, 27, 28, 29, or 30, further comprising:
- actuating a release latch of the retractor to release the blade head from the receptacle;
- removing the retractor from the exposure; and
- removing the retractor blade from the exposure.

Embodiment 33: A surgical retractor comprising:
- a first blade engagement having a blade receptacle defined in a first end of a body of the first blade engagement, the blade receptacle having an opening that narrows to a seat for receiving a blade head, the seat defining a shape that reduces translation, rotation, and/or angulation of the blade head; and
- a first retractor blade having an elongate portion extending from a retractor head, the retractor head configured and shaped to be received by the blade receptacle of the first blade engagement.

Embodiment 34: The surgical retractor of embodiment 33, further comprising:
- a second blade engagement having a blade receptacle defined in a first end of a body of the second blade engagement, the blade receptacle having an opening that narrows to a seat for receiving a blade head, the seat defining a shape that reduces translation, rotation, and/or angulation of the blade head; and
- a second retractor blade having an elongate portion extending from a retractor head, the retractor head configured and shaped to be received by the blade receptacle of the second blade engagement.

Embodiment 35: The surgical retractor of either one of embodiments 33 or 34, wherein the seat of the first and/or second blade engagement comprises an upper conical portion and a lower conical portion.

Embodiment 36: The surgical retractor of embodiment 35, wherein the upper conical portion and the lower conical portion are connected via a cylindrical portion.

Embodiment 37: The surgical retractor of embodiment 36, wherein at least a portion of the cylindrical portion comprises a planar surface.

ADDITIONAL TERMS AND DEFINITIONS

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It should also be noted that some of the embodiments disclosed herein may have been disclosed in relation to a particular surgical tool (e.g., a blade with a blade head); however, other surgical tools (e.g., scalpels, brushes, handles, etc.) are also contemplated. Structures of the retractor are referred to as more "proximal" when they interface with the jaw or head portion of a patient, while structures that extend toward the lower half of a patient are referred to as more "distal."

In one embodiment, the terms "about" and "approximately" refer to numerical parameters within 10% of the indicated range. The terms "a," "an," "the," and similar referents used in the context of describing the embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the author(s) of this disclosure for carrying out the embodiments disclosed herein. Of course, variations on these described embodiments will become apparent to those of ordinary skill in the art upon reading the foregoing description. The author(s) expects skilled artisans to employ such variations as appropriate, and the author(s) intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

Although this disclosure provides many specifics, these should not be construed as limiting the scope of any of the claims that follow, but merely as providing illustrations of some embodiments of elements and features of the disclosed subject matter. Other embodiments of the disclosed subject matter, and of their elements and features, may be devised which do not depart from the spirit or scope of any of the claims. Features from different embodiments may be employed in combination. Accordingly, the scope of each claim is limited only by its plain language and the legal equivalents thereto.

What is claimed:

1. A retractor comprising:

a proximal portion having a rack and pinion mechanism in connection with a first cabin and a second cabin such that the first and second cabins are independently retractable along the rack, the rack having a first adaptor on a first end and a second adaptor on a second end, the first and second adaptors for selectively connecting the rack to a table-mounted surgical arm;

a distal portion opposite the proximal portion, the distal portion connected to the proximal portion through a first arm in connection with the first cabin and a second arm in connection with the second cabin, the distal portion having a first blade engagement in connection with the first arm and a second blade engagement in connection with the second arm, wherein the first and second blade engagements each comprise:

a receiving body in connection with the first arm or second arm, respectively, a receptacle defined in a first end of the receiving body, the receptacle having an hourglass shape for receiving a blade head, a latch for covering a portion of the receptacle upon receipt of the blade head, an adaptor at a second end of the receiving body, the adaptor for selectively connecting the distal portion to a table-mounted surgical arm, a release latch for retracting the latch, and an angulation knob adjacent to the adaptor at the second end of the receiving body, the angulation knob for rotating the receiving body.

2. The retractor of claim 1, wherein the hourglass shape of the receptacle prevents rotation, translation, and angulation of the blade head when the blade head is received within the receptacle.

3. The retractor of claim 1, wherein the angulation knob angularly rotates the receiving body of the first and second blade engagements about a longitudinal axis of the first and second arms, respectively.

4. The retractor of claim 1, wherein the first arm is hingedly connected to the first cabin at a proximal end of the first arm and is hingedly connected to the first blade engagement at a distal end of the first arm.

5. The retractor of claim 1, wherein the receptacle of the first blade engagement comprises a top conical portion, a bottom conical portion, and a planar cylindrical neck connecting the top conical portion to the bottom conical portion to form the hourglass shape.

6. The retractor of claim 5, wherein the neck defines an opening of the receptacle for receiving a blade head and wherein the latch extends across at least a portion of the opening when covering the receptacle.

7. The retractor of claim 1, wherein the blade head comprises an hourglass shape corresponding to the hourglass shape of the receptacle.

8. The retractor of claim 1, wherein the rack and pinion mechanism comprises:

a first pinion for retracting the first cabin along the rack;

a first pawl for securing a position of the first cabin along the rack;

a second pinion for retracting the second cabin along the rack; and a second pawl for securing a position of the second cabin along the rack.

9. The retractor of claim 8, wherein the first and second pawls prevent inward motion of the first and second cabins, respectively, without actuating the first and second pawl.

10. The retractor of claim 1, wherein the retractor comprises a zero- or home position indicator for determining a home or zero position of the retractor.

11. The retractor of claim 1, wherein the rack comprises a zero-position indicator for determining a zero position of the retractor.

12. The retractor of claim 1, wherein the latch for covering the receptacle upon receipt of the blade head comprises a spring-loaded rod housed within a channel and mechanically connected to the release latch.

13. The retractor of claim 1, wherein the latch for closing the receptacle upon receipt of the blade head is biased towards and partially across an opening of the receptacle.

14. The retractor of claim 13, wherein the latch comprises:

a rod housed within a channel, the rod having a chamfered face over which the blade head slides as the blade head enters the receptacle; and a spring within the channel biasing the rod towards the opening of the receptacle, wherein the rod retracts into the channel as the blade head slides on the chamfered face, and wherein the rod returns to its bias position and locks the blade head within the receptacle when the blade head passes the rod and is received within the receptacle.

15. A retractor comprising:

a proximal portion; and a distal portion opposite the proximal portion, the distal portion comprising:

a first blade engagement having a blade receptacle defined in a first end of a body of the first blade engagement, the blade receptacle having a lateral opening that narrows to a seat for receiving a shaped blade head, the seat comprising an upper conical portion, a lower conical portion connected to the upper conical portion by a planar and/or cylindrical side wall; and a second blade engagement having a blade receptacle defined in a first end of a body of the second blade engagement, the blade receptacle having a lateral opening that narrows to a seat for receiving a blade head, the seat defining a shape that constrains translation, rotation, and/or angulation of the blade head.

16. The retractor of claim 15, wherein the upper conical portion is connected to the lower conical portion via a planar and/or cylindrical portion.

17. The retractor of claim 16, wherein the planar and/or cylindrical portion at least partially defines the opening and the planar and/or cylindrical portion comprises a first flat portion, a U-shaped portion, and a second flat portion opposite the first flat portion.

18. The retractor of claim 16, wherein the planar and/or cylindrical portion defines a void into which a latch may extend to at least partially close the blade receptacle of the first blade engagement upon receipt of a blade head, thereby locking the blade head within the blade receptacle and reducing translation of the blade head relative to the retractor.

19. The retractor of claim 15, wherein the seat of the second blade engagement comprises an upper conical portion, a lower conical portion connected to the upper conical portion by a planar and/or cylindrical side wall.

* * * * *